(12) United States Patent
Cannon, Jr. et al.

(10) Patent No.: US 7,846,103 B2
(45) Date of Patent: Dec. 7, 2010

(54) PROBE GUIDE FOR USE WITH MEDICAL IMAGING SYSTEMS

(75) Inventors: Charles Cannon, Jr., Jersey Shore, PA (US); David Hull, West Hartford, CT (US); William R. Camerer, III, Jersey Shore, PA (US)

(73) Assignee: Medical Equipment Diversified Services, Inc., Jersey Shore, PA (US)

( * ) Notice: Subject to any disclaimer, the term of this patent is extended or adjusted under 35 U.S.C. 154(b) by 1327 days.

(21) Appl. No.: 11/122,640

(22) Filed: May 5, 2005

(65) Prior Publication Data

US 2006/0064010 A1 Mar. 23, 2006

Related U.S. Application Data

(60) Provisional application No. 60/611,123, filed on Sep. 17, 2004.

(51) Int. Cl.
*A61B 8/00* (2006.01)
*A61B 8/14* (2006.01)

(52) U.S. Cl. .......................... 600/461; 600/437; 600/464

(58) Field of Classification Search ......... 600/437–464, 600/424; 606/130
See application file for complete search history.

(56) References Cited

U.S. PATENT DOCUMENTS

| | | | |
|---|---|---|---|
| 3,538,915 A | 11/1970 | Frampton et al. | 128/214 |
| 4,230,118 A | 10/1980 | Holman et al. | 128/314 |
| 4,397,438 A | 8/1983 | Chapman | 248/229 |
| 4,402,324 A | 9/1983 | Lindgren et al. | 128/660 |
| 4,408,611 A | 10/1983 | Enjoji | 128/660 |
| 4,469,106 A * | 9/1984 | Harui | 600/461 |
| 4,491,137 A | 1/1985 | Jingu | 128/660 |
| 4,504,269 A | 3/1985 | Durand | 604/272 |
| 4,542,747 A | 9/1985 | Zurinski et al. | 128/660 |
| 4,628,929 A | 12/1986 | Intengan et al. | 128/314 |
| 4,635,644 A | 1/1987 | Yagata | 128/660 |
| 4,899,756 A | 2/1990 | Sonek | 128/660.05 |
| 5,052,396 A | 10/1991 | Wedel et al. | 128/662.05 |
| 5,076,279 A | 12/1991 | Arenson et al. | 128/662.05 |
| 5,160,105 A | 11/1992 | Miller | 690/374 |
| 6,595,933 B2 * | 7/2003 | Sarvazyan et al. | 600/587 |
| 6,695,786 B2 * | 2/2004 | Wang et al. | 600/461 |
| 6,799,065 B1 * | 9/2004 | Niemeyer | 600/407 |
| 2002/0120188 A1 * | 8/2002 | Brock et al. | 600/407 |
| 2003/0105410 A1 * | 6/2003 | Pearlman | 600/547 |
| 2005/0049486 A1 * | 3/2005 | Urquhart et al. | 600/429 |

* cited by examiner

*Primary Examiner*—Long V Le
*Assistant Examiner*—Sanjay Cattungal
(74) *Attorney, Agent, or Firm*—David Aker

(57) ABSTRACT

An improved probe guide and probe guide system for use in conjunction with a medical imaging device is disclosed. The medical imaging device may be any type of imaging device that generates a cross-sectional image of a portion of a patient's body in a single image plane, such as, ultrasound, CT, or MRI imaging devices. The probe guide allows maintaining the movement of the probe within the image plane and accurate placement of a probe, such as a biopsy needle, by allowing a range of angular translation of the probe. The probe guide system enables extrapolation of the penetration path of the probe held by the probe guide and superimpose it on to the cross-sectional image allowing the medical personnel to view the penetration path of the probe within the patient in advance.

3 Claims, 25 Drawing Sheets

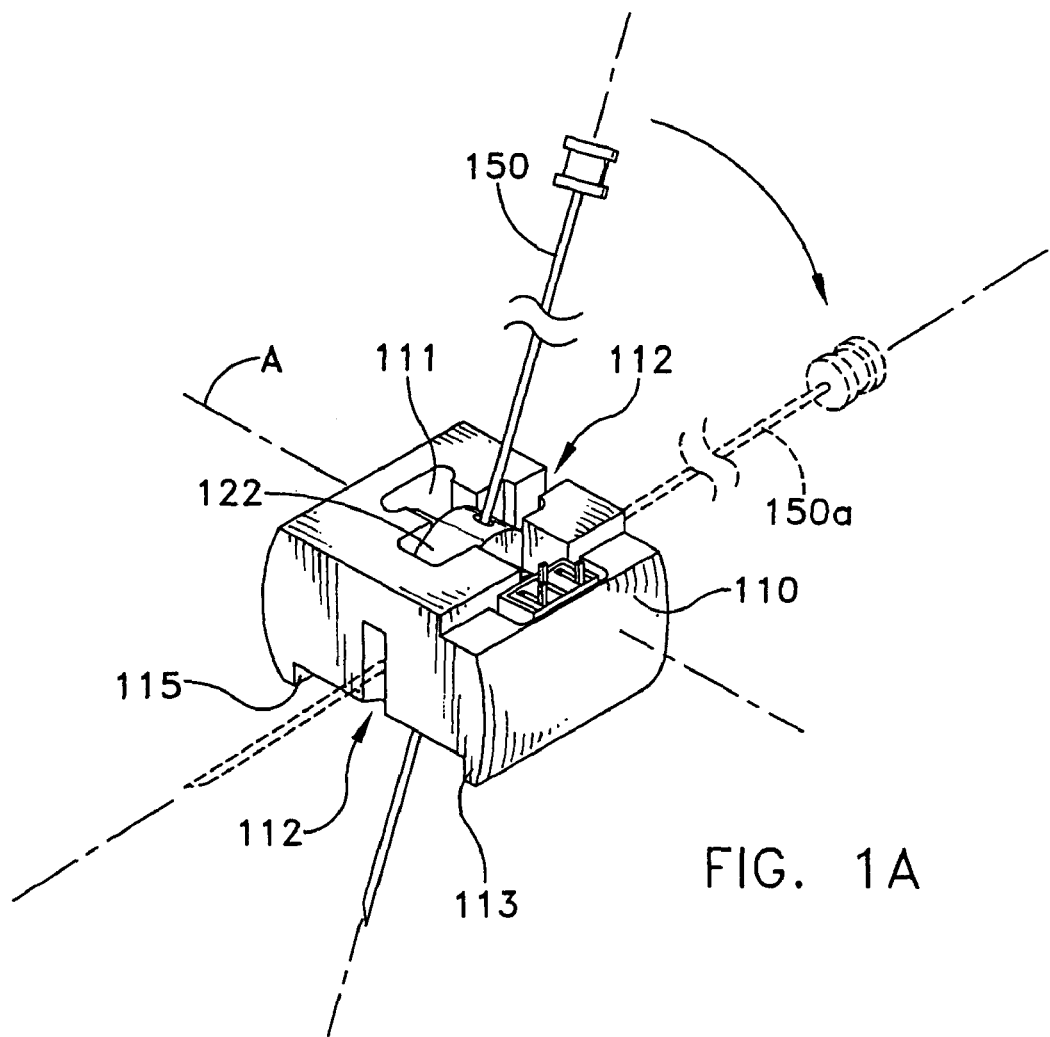
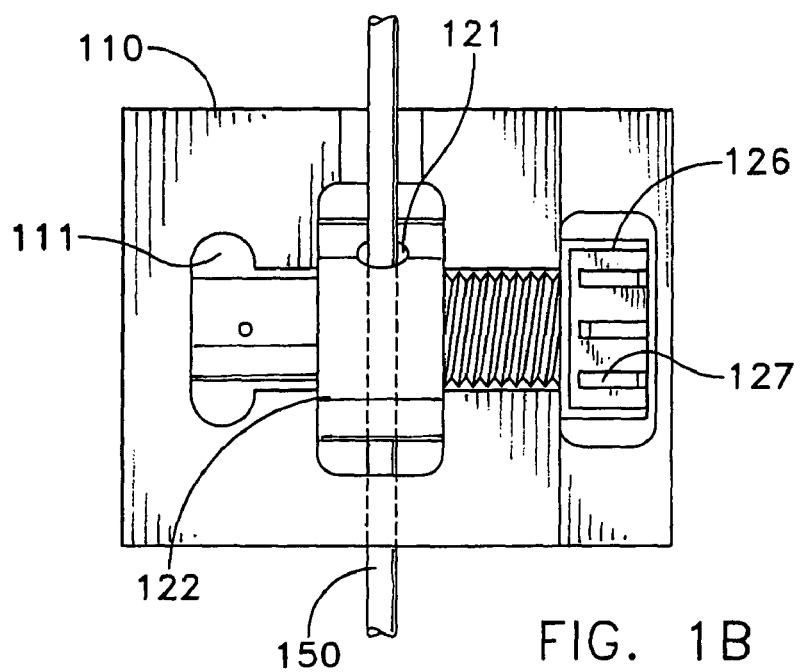
FIG. 1A
FIG. 1B

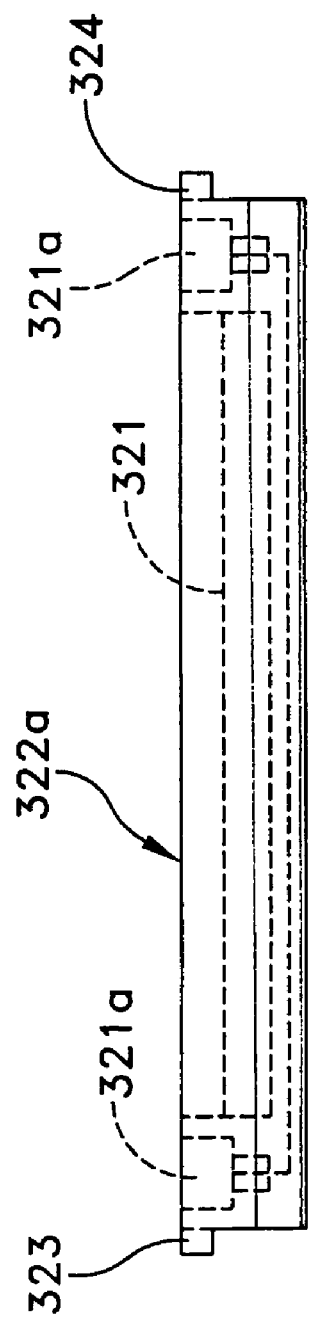
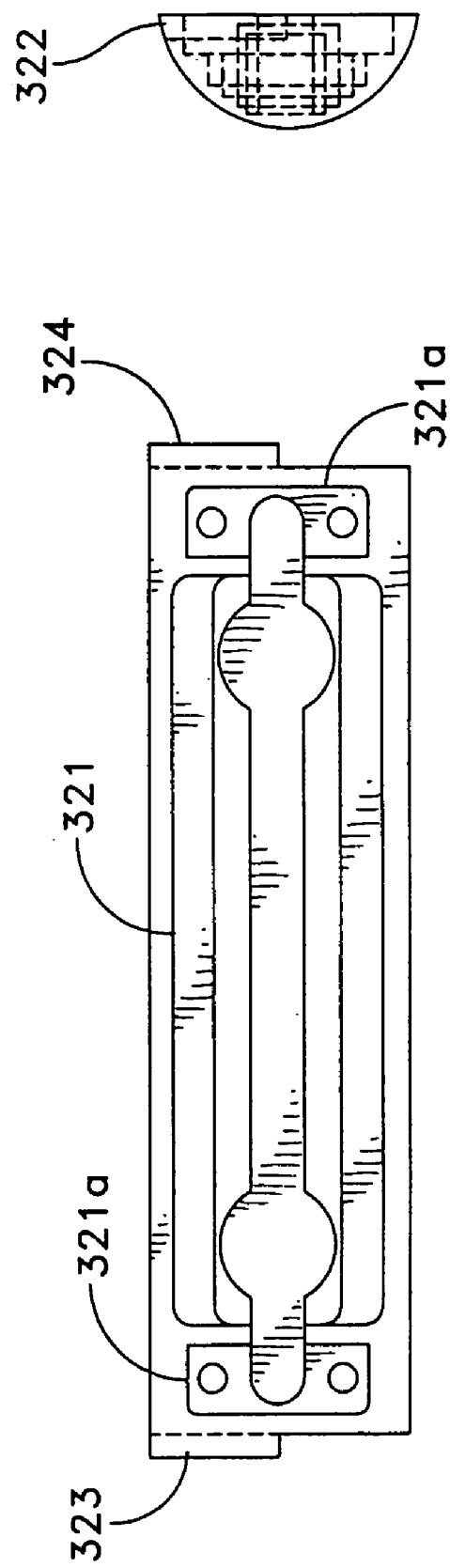
FIG. 3G
FIG. 3H
FIG. 3I

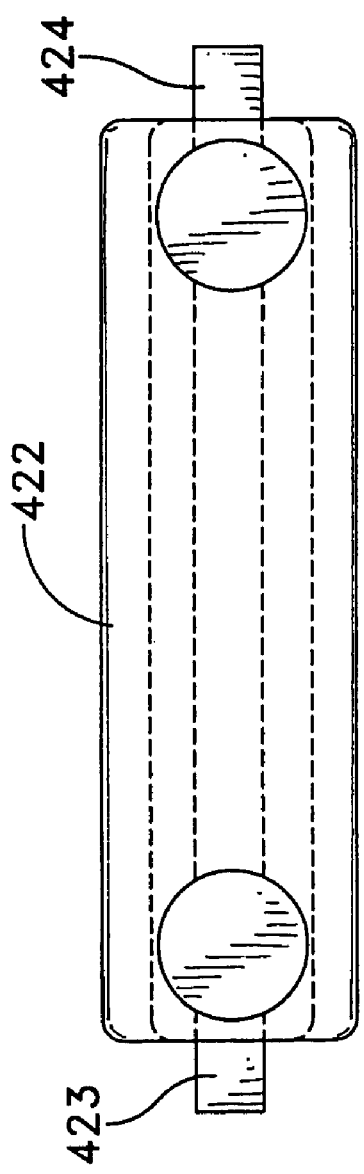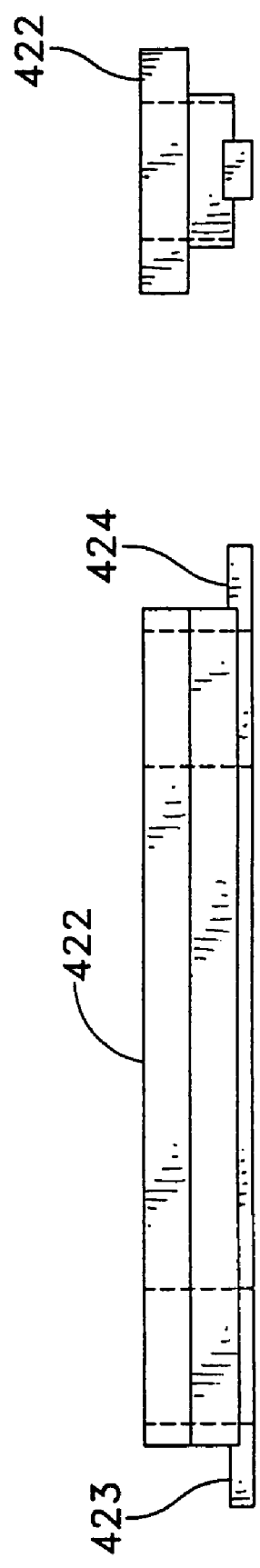
FIG. 3J
FIG. 3K
FIG. 3L

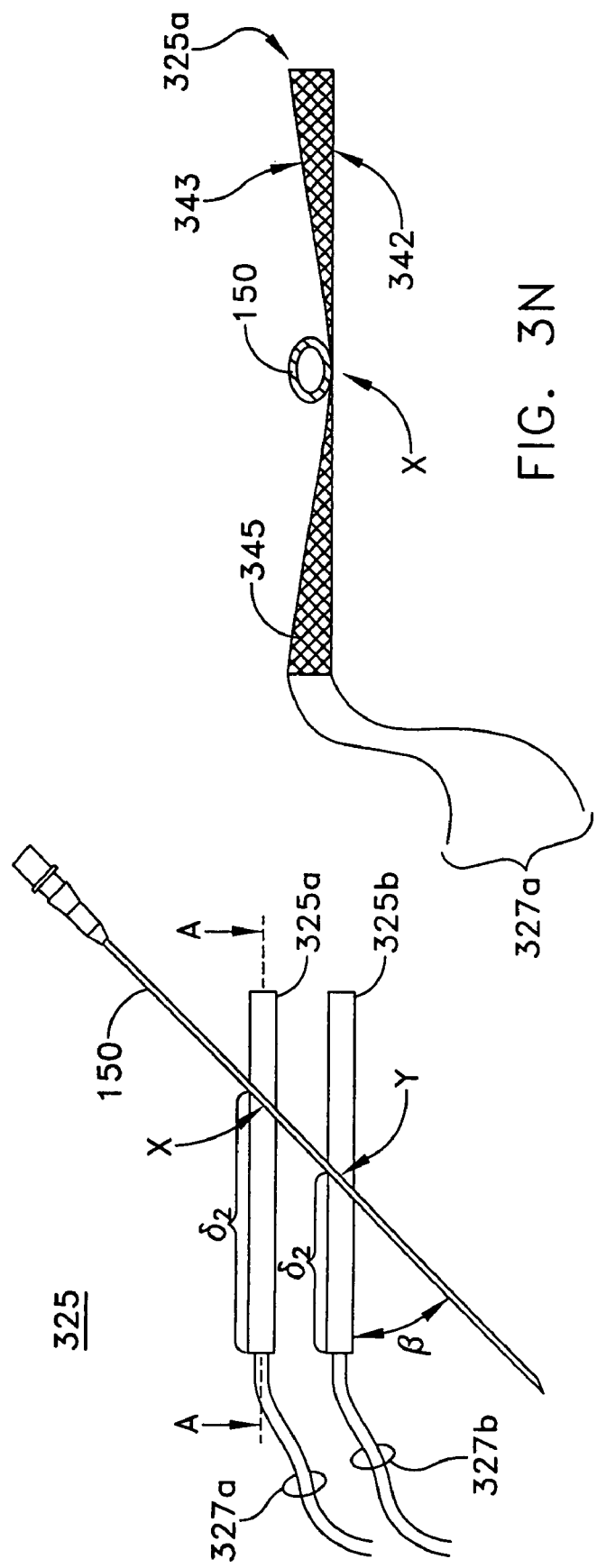

PROBE GUIDE FOR USE WITH MEDICAL IMAGING SYSTEMS

CROSS-REFERENCE TO RELATED APPLICATIONS

This application claims the benefit of U.S. Provisional patent application Ser. No. 60/611,123, filed on Sep. 17, 2004, which is incorporated herein by reference.

FIELD OF THE INVENTION

The invention relates to a probe guide that can be utilized with different modes and models of single plane medical imaging devices, such as, ultrasound, computer aided tomography (CT), and magnetic resonance imaging (MRI).

BACKGROUND OF THE INVENTION

It is well known in the medical industry that single plane imaging systems are useful for performing the localizing of specific tissues for procedures such as biopsies, and the destruction of diseased tissues using various clinical techniques such as heat, cold, and chemical applications. In such procedures, the placement of therapeutic probes, guided by imaging devices, are used. Advantageously, the needle or probe is visible during the surgical procedure.

In the past, a biopsy or therapeutic devices, such as, biopsy probe or needle, was inserted freehand or a fixed plane biopsy guide was used to aid in positioning and holding the therapeutic device. Such fixed plane biopsy guide was generally rigidly attached to the imaging device and was limited to the geometry of the imaging device. The targeted areas were limited to the design of the imaging device.

Thus, an improved probe guide that will allow accurate placement of a probe is desired.

SUMMARY OF THE INVENTION

According to an embodiment of the invention, an improved probe guide for use in conjunction with a medical imaging device is disclosed. The medical imaging device may be any type of imaging device that generates a cross-sectional image of a portion of a patient's body in a single image plane, such as, ultrasound, CT, or MRI imaging devices. The probe guide of the invention allows accurate placement of a probe, such as a biopsy needle, by allowing a range of angular translation of the probe.

The probe guide for use in conjunction with a medical imaging device may comprise a probe guide body having a connecting mechanism for connecting the probe guide to the medical imaging device. A probe holder for holding a probe is provided in the probe guide body that will hold the probe and allow angular and axial translations of the probe while maintaining the probe within the image plane when the probe guide is connected to the imaging device. The probe holder includes an encoder incorporated therein for detecting the angular orientation of the probe relative to the image plane. The angular orientation of the probe measured by the encoder is used to extrapolate or project the probe's penetration path and superimpose the projected penetration path of the probe on to the cross-sectional image formed by the medical imaging device.

According to another aspect of the invention, an articulating probe guide for use in conjunction with a medical imaging device is disclosed. The imaging device generates a cross-sectional image of a portion of a patient's body in an image plane. The articulating probe guide comprises an imaging device holder having a connecting mechanism for connecting the medical imaging device to the imaging device holder. A handle (hereinafter referred to as a probe guide body) is pivotally connected to the imaging device holder by a hinge. A probe holder for holding a probe is provided in the probe guide body and the probe holder is adapted and configured to allow angular and axial translations of the probe within the image plane of the cross-sectional image of a portion of the patient's body when the imaging device holder is connected to the imaging device.

A first encoder is incorporated into the hinge and the first encoder is used for detecting angular orientation of the imaging device holder relative to the probe guide body. The probe holder has a second encoder incorporated therein for detecting angular orientation of the probe relative to the probe guide body and the linear position of the probe within the probe guide body. This effectively provides information about the position of the probe relative to the image plane. The probe holder of this embodiment of the invention allows accurate placement of a probe, such as a biopsy needle, by allowing a range of both angular and lateral translation of the probe. The angular orientation and the lateral position of the probe is used to extrapolate or project the probe's penetration path and superimpose the penetration path on to the cross-sectional image formed by the medical imaging device to guide the physician.

According to yet another aspect of the invention, a probe guide system for use in conjunction with a medical imaging device comprises a probe guide which includes a probe guide body having a connecting mechanism for connecting the probe guide to the medical imaging device. A probe holder for holding a probe is provided in the probe guide body adapted and configured to allow angular and axial translations of the probe within the image plane when the probe guide is connected to the imaging device. The probe holder has an encoder incorporated therein, for detecting angular orientation of the probe relative to the image plane. The probe guide system also includes a processing unit including a video input port and a video output port. The processing unit extrapolates or projects the probe's penetration path from the angular orientation of the probe detected by the encoder and superimposes the projected penetration path on to the cross-sectional image received from the medical imaging device through the video input and transmits a superimposed image through the video output port to a video display unit.

According to yet another aspect of the invention, a probe guide system for use in conjunction with a medical imaging device comprises an articulating probe guide and a processing unit. The articulating probe guide comprises an imaging device holder having a connecting mechanism for connecting the medical imaging device to the imaging device holder. A probe guide body is pivotally connected to the imaging device holder by a hinge. A probe holder for holding the probe is provided in the probe guide body and the probe holder is adapted and configured to allow angular and axial translations of the probe within the image plane when the imaging device holder is connected to the imaging device.

A first encoder is incorporated into the hinge for detecting angular orientation of the imaging device holder relative to the probe guide body. The probe holder has a second encoder incorporated therein for detecting angular orientation of the probe relative to the probe guide body and the linear position of the probe within the probe guide body. The probe guide system also includes a processing unit including a video input port and a video output port. The processing unit includes a video input port and a video output port. The processing unit extrapolates or projects the probe's penetration path from the angular orientation of the probe detected by the second encoder and superimposes the projected penetration path on to the cross-sectional image received from the medical imaging device through the video input port and transmits a superimposed image through the video output port to a video display unit.

A benefit of the probe guide of the invention is that it allows accurate placement of a probe, such as a biopsy needle, by allowing a range of angular translation as well as axial translation of the probe.

BRIEF DESCRIPTION OF THE DRAWINGS

The following schematic illustrations will be used to describe the various exemplary embodiments of the invention in more detail. These drawings are not intended to show actual dimensions or proportions. Like reference numbers in figures represent like parts.

FIG. 1A is a isometric view of a probe guide body of the probe guide of FIG. 1, assembled with a probe holder and the associated encoder.

FIG. 1B is a top view of the assembled probe guide body of FIG. 1A.

FIGS. 3G, 3H, and 3I illustrate side view, plan view, and an end view, respectively, of the probe holder 322 (slide housing) of FIG. 3.

FIGS. 3J, 3K, and 3L illustrate plan view, side view, and an end view, respectively, of the face plate 422 that attaches to the probe-facing side of the probe holder 322.

FIG. 3M is an illustration of the pair of sensor strips 327a and 327b of the probe guide 300.

FIG. 3N is a cross sectional view along the line A-A of the sensor strip 327a.

FIG. 3O is an illustration of the probe guide 300 of FIG. 3 fully assembled and being used in conjunction with an ultrasound transducer 390 and a probe needle 150 in which the probe guide 300 is in straight configuration, i.e. $\alpha=180°$.

DETAILED DESCRIPTION

Figure 1:
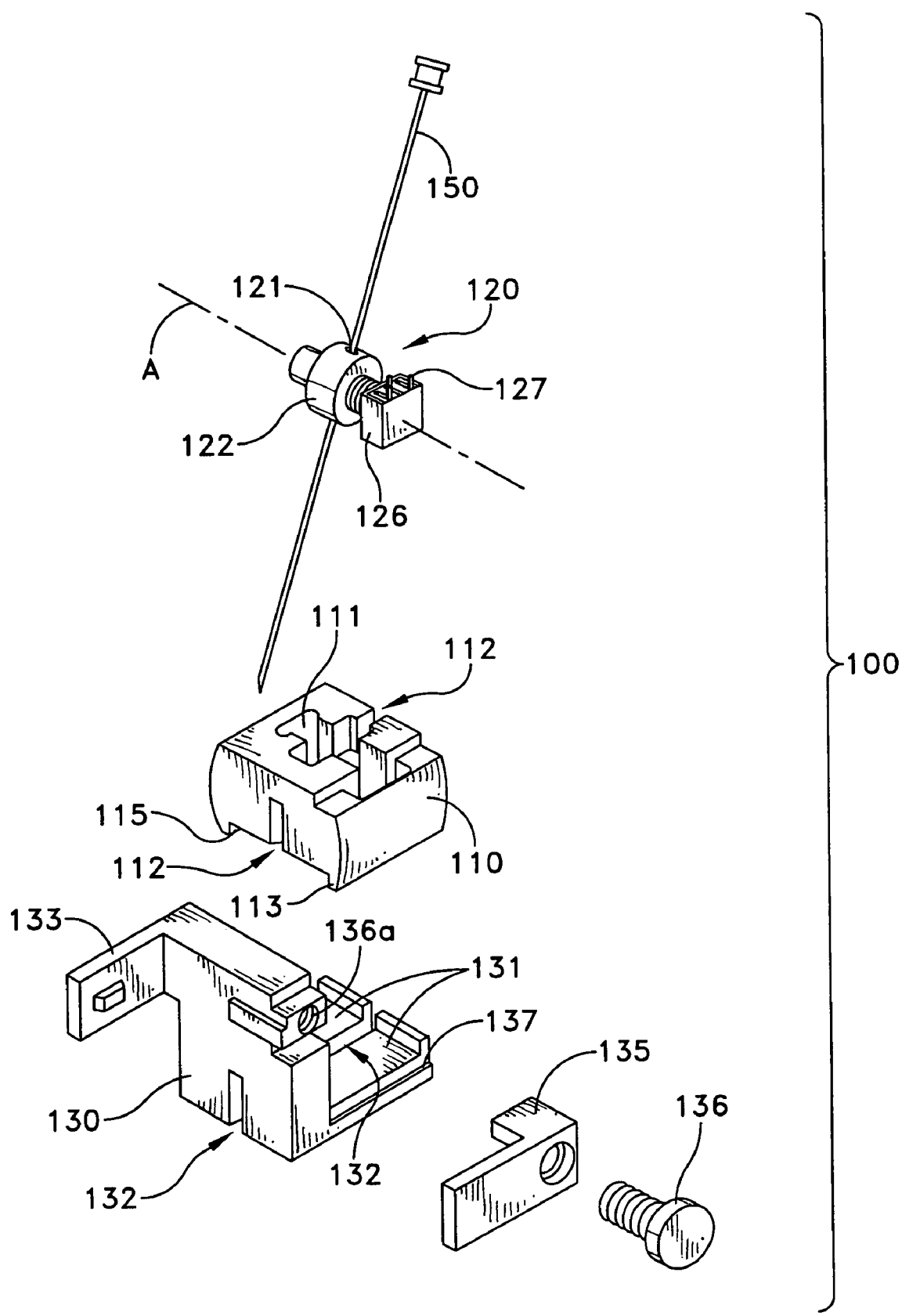
FIG. 1 is an exploded isometric view of a probe guide according to an embodiment of the invention.
Figure 1C:
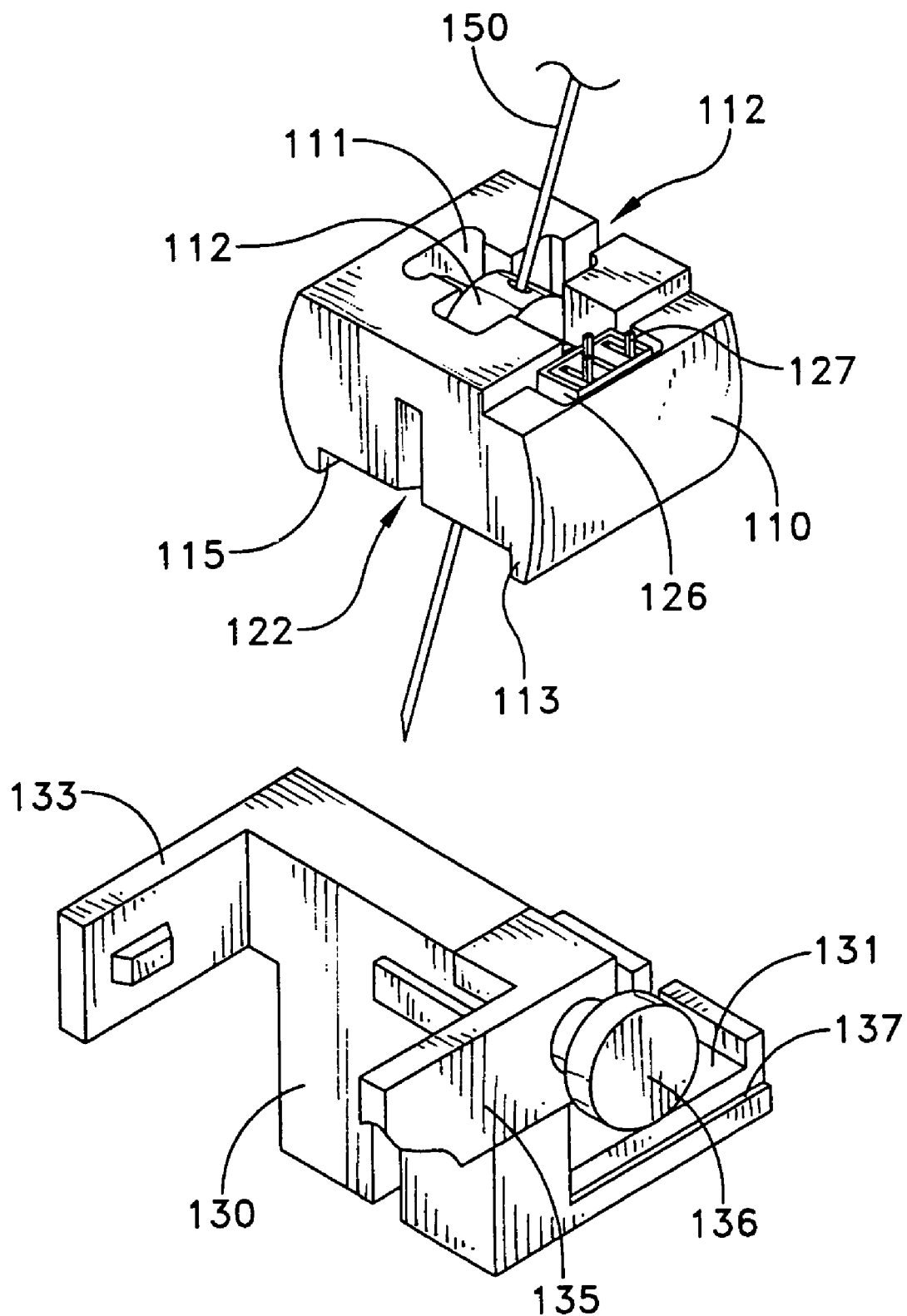
FIG. 1C is an exploded isometric view of the probed guide body and a connecting mechanism from FIG. 1.
Figure 1D:
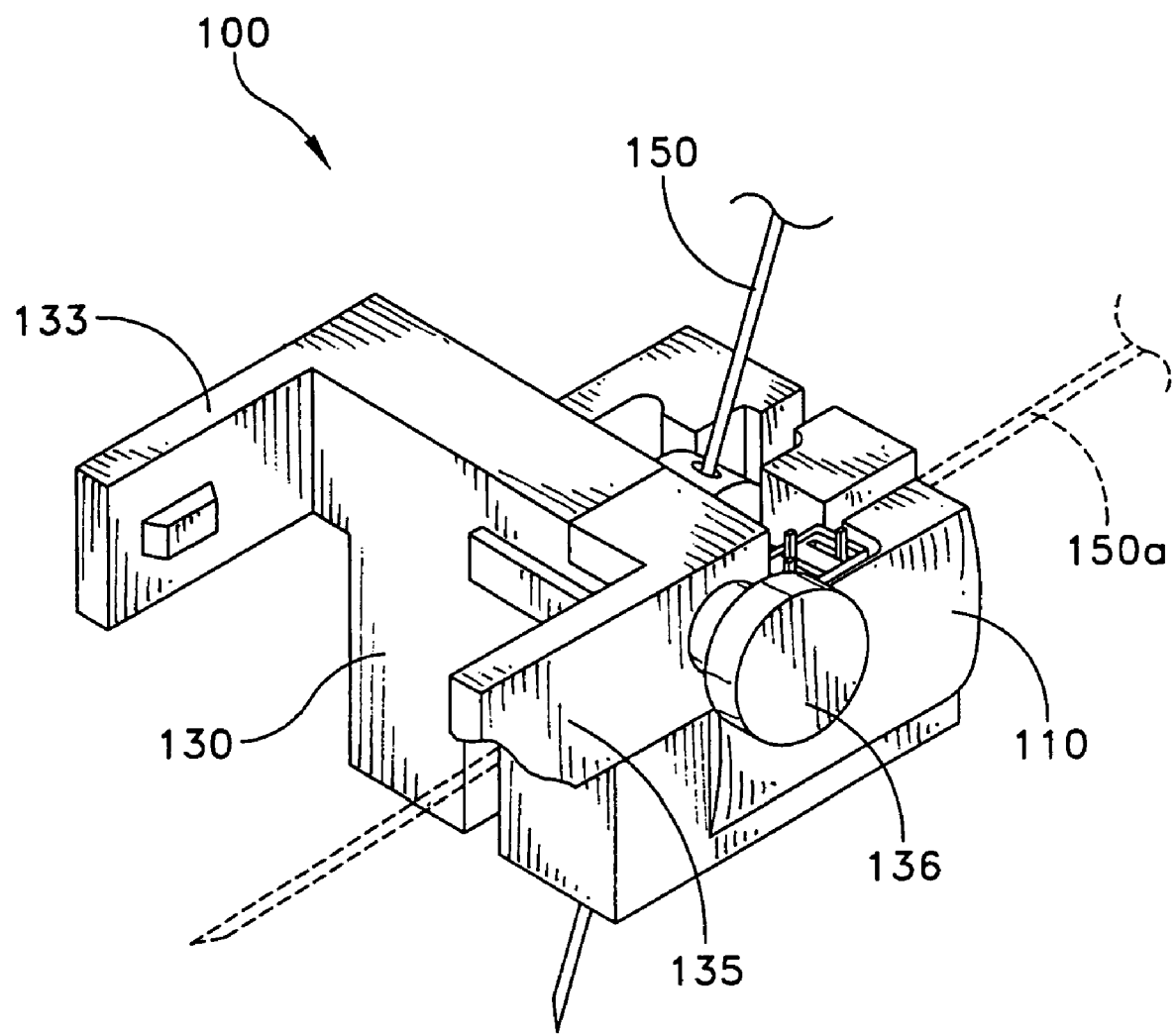
FIG. 1D is a isometric view of a fully assembled probe guide of FIG. 1.
Figure 1E:
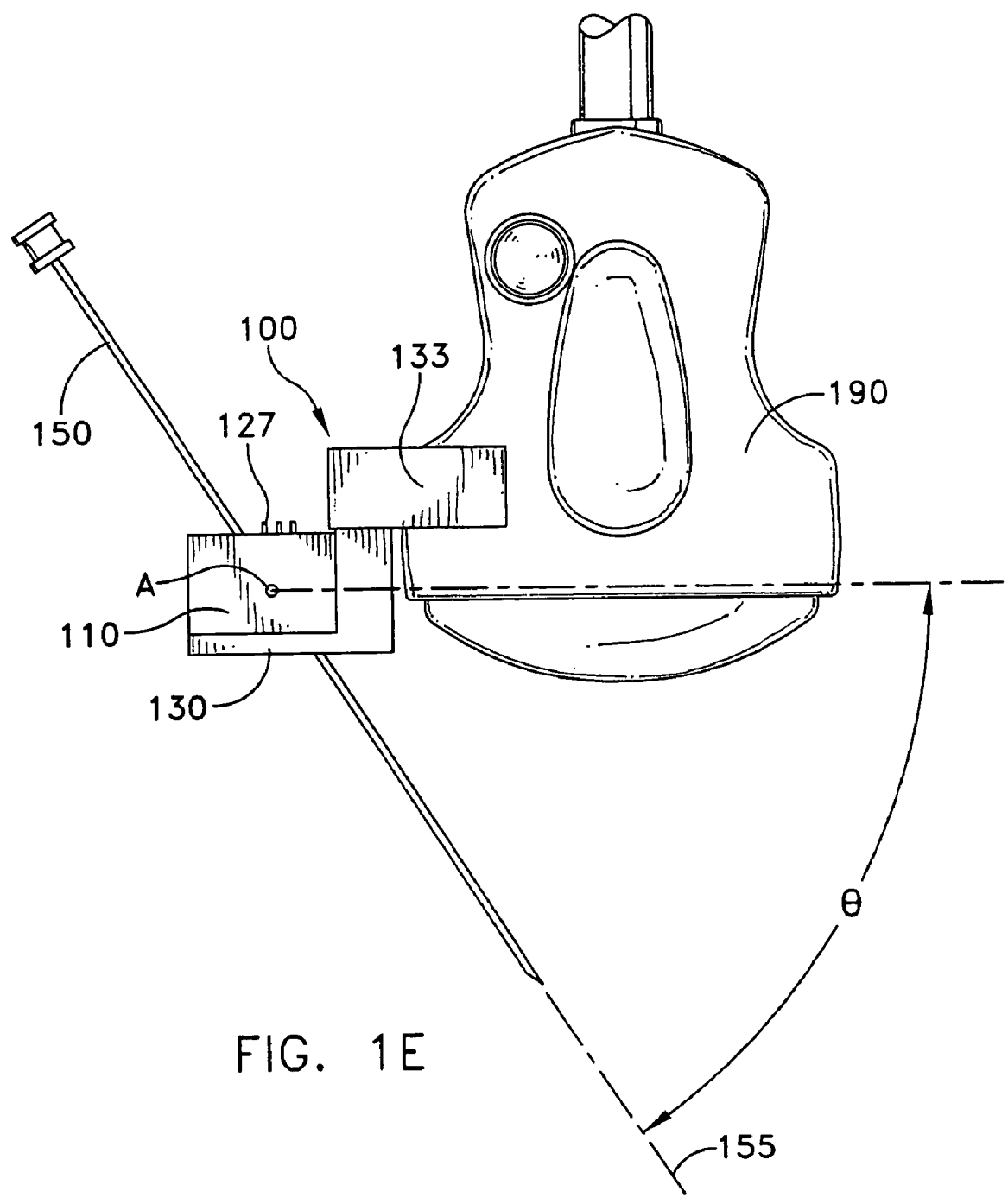
FIG. 1E is a side view of the probe guide of FIGS. 1 and 5 connected to an ultrasound transducer.
Figure 1F:
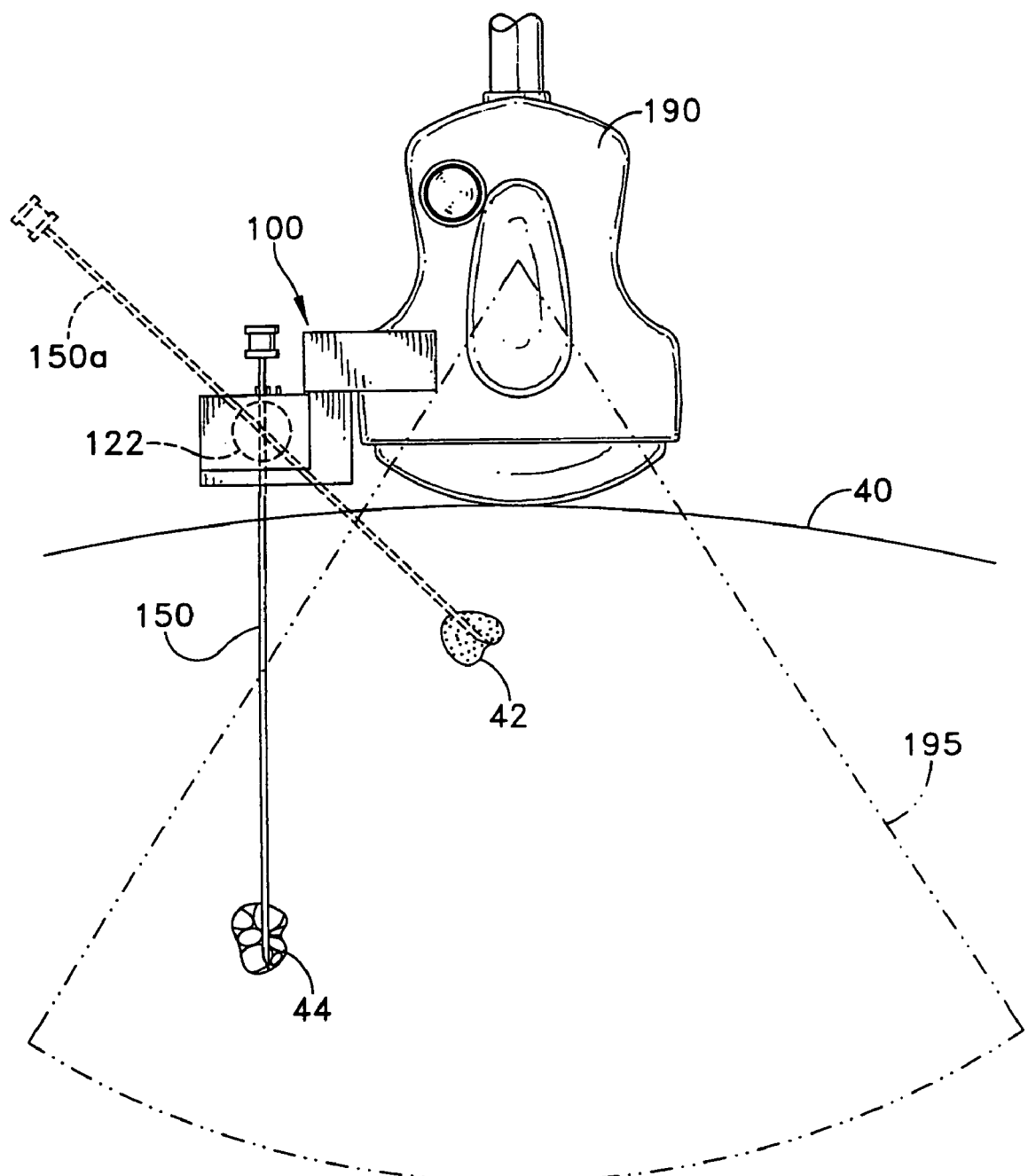
FIG. 1F is another view of the probe guide and ultrasound transducer assembly of FIG. 1E illustrating an exemplary range of angular and axial displacement possible with the probe guide of FIGS. 1 and 1D in relation to the image plane of the ultrasound transducer of FIG. 1E.

Referring to FIGS. 1-1F, disclosed herein is a probe guide 100 for use in conjunction with a medical imaging device 190, according to an embodiment of the invention. The medical imaging device 190 illustrated in this example is an ultrasound transducer but the various embodiments of the probe guide may be used in conjunction with any type of imaging device that generates a cross-sectional image of a portion of a patient's body in a single image plane, such as, ultrasound, CT, or MRI imaging devices.

FIG. 1 is an exploded view of the probe guide 100. The probe guide 100 may comprise a probe guide body 110 having a connecting mechanism 130 for connecting the probe guide 100 to the medical imaging device 190 (shown in FIGS. 1E and 1F). A probe holder 120 for holding a probe 150 is provided in the probe guide body 110. The probe guide body 110 has a cavity 111 for receiving the probe holder 120. FIG. 1A illustrates an assembled probe guide body 110 with the probe holder 120 placed within the cavity 111.

The probe holder 120 includes a rotating member 122 and an encoder 126. The rotating member 122 rotates about its rotational axis A. The rotating member 122 has a hole 121 bored therethrough for receiving the probe 150. The hole 121 a diameter which would allow a particular probe 150 to fit snuggly so that a user can manipulate the probe 150 in and out of the hole 121 in a sliding action with ease, yet hold the probe 150 in place so that the probe would not slide within or fall out of the hole 121 by itself.

The hole 121 is bored through the rotating member 122 so that the hole 121 is transverse to and intersects the rotational axis A of the rotating member 122. The encoder 126 and the rotational member 122 is rotationally engaged so that the encoder may be used to detect the angular orientation of the rotational member 122 which, in turn, will represent the angular orientation of the probe 150 placed in the hole 121. The encoder 126 may be a potentiometer-type whose electrical resistance changes proportionally with the angular orientation of the rotational member 122. Because the hole 121 is transverse to and intersects the rotational axis A of the rotational member 122, the angular orientation of the rotational member 122 represents the angular orientation of the probe placed in the hole 121. The encoder 126 generally includes a connector 127 for electrically connecting the encoder 126 to a processing unit 500 (shown in FIGS. 4 and 5) of a probe guide system so that the processing unit may monitor the angular orientation of the probe 150 through the encoder 126. In this example, the processing unit would monitor the electrical resistance of the encoder 126 and determine the particular angular orientation of the probe 150 at a given moment.

As illustrated in FIG. 1B, the probe guide body 110 is preferably provided with a channel 112 to allow maximum rotational movement of the probe 150. The probe 150 may be adjusted between a vertical position to almost horizontal position represented by a dotted line figure of the probe 150a.

The exploded view in FIG. 1 illustrates the details of the components of the connecting mechanism 130. The connecting mechanism 130 may comprise a base portion 131 for receiving the probe guide body 110. The base portion 131 has a ledge 137 along its sides (the ledge on the far side of the base portion 131 in FIG. 1 is not visible) for engaging the bottom flanges 113 and 115 of the probe guide body 110. FIG. 1E shows the probe guide body 110 engaged with the connecting member 130. The connecting member 130 is provided with a channel 132 that corresponds with the channel 112 of the probe guide body 110 to allow the probe 150 to be manipulated through its full range of angular orientation. This is better illustrated in the assembled isometric view of the probe guide body 110 and the connecting member 130 shown in FIG. 1D. The probe 150 is shown in its second nearly horizontal position 150a in dotted lines. As shown, the channel 132 allows the probe 150 to be manipulated within its rotational range.

Arms 133, 135 may be used to connect the connecting member 130 to the medical imaging device 190. One arm 133 is formed as an integral part of the connecting member 130 and the second arm 135 may be provided as a separate piece and secured to the connecting member 130 by a screw 136 which threads into the screw hole 136a. FIG. 1D illustrates the second arm 135 secured to the connecting member 130 using the screw 136. When attaching the connecting member 130 to the medical imaging device 190, the connecting member 130 would generally be placed in position against the medical imaging device 190 first and then the second arm 135 is secured onto the connecting member 130 using the screw 136 to securely attach the connecting member 130 to the medial imaging device 190. FIGS. 1E and 1F illustrate the fully assembled probe guide 100 attached to the medical imaging device 190.

In this example, the arms 133, 135 are used to clamp the connecting member 130 to the medical imaging device 190. The mechanical arrangement shown is only an example and it would be obvious to one of ordinary skill in the art that the mechanical engagement between the connecting member 130 and the medical imaging device 190 may be achieved in many different configurations. For example, the arms 133, 135 may be spring-biased like the jaws of an alligator clip and clamp on to the medical imaging device 190. The particular method or mechanical arrangement of attaching the probe guide 100 to the medical imaging device 190 may be varied to accommodate the needs of a particular application and are all within the scope of the various embodiments contemplated for the probe guide of the invention.

FIG. 1F illustrates the assembled probe guide 100 attached to a medical imaging device 190, in this case, an ultrasound transducer model B-K 8665, and the benefit of using the probe guide 100 of the invention. Associated with the imaging device 190 is its image plane 195.

In an actual medical application, the medical imaging device 190 would be placed against a patient's body 40 in order to view an area inside a patient's body into the image plane 195. The areas 42 and 44 represent areas inside the patient's body 40 that are the intended target of probing or examination. For example, the areas 42 and 44 may be areas where suspected diseased tissues are located inside the patient's body 40 and the probe 150 may be a biopsy needle.

The probe 150 guided by the probe guide 100 may be manipulated both axially and rotationally to reach the areas 40 and 42 as illustrated. The area 40 may be reached by fully axially extending the probe 150 in a vertical position. The area 42 may be reached by only partially extending the probe in axial direction and rotating the probe to the second position 150a represented by dotted lines. According to the invention, because the rotational axis A (see FIG. 1E) of the rotating member 122 is transverse to the image plane 195 of the medical imaging device 190 and the probe 150 is held in the hole 121 of the rotating member 122, which is oriented transverse to the rotational axis A and intersects the rotational axis A, the probe 150 remains in the image plane 195 of the medical imaging device 190 throughout the probe's full range of motion.

The probe holder 120 includes an encoder 126 incorporated therein for detecting the angular orientation of the probe 150 relative to the image plane of the medical imaging device 190. The angular orientation of the probe measured by the encoder 126 is used to extrapolate or project the probe's penetration path and superimpose the projected penetration path of the probe on to the cross-sectional image formed by the medical imaging device 190.

Figure 2:
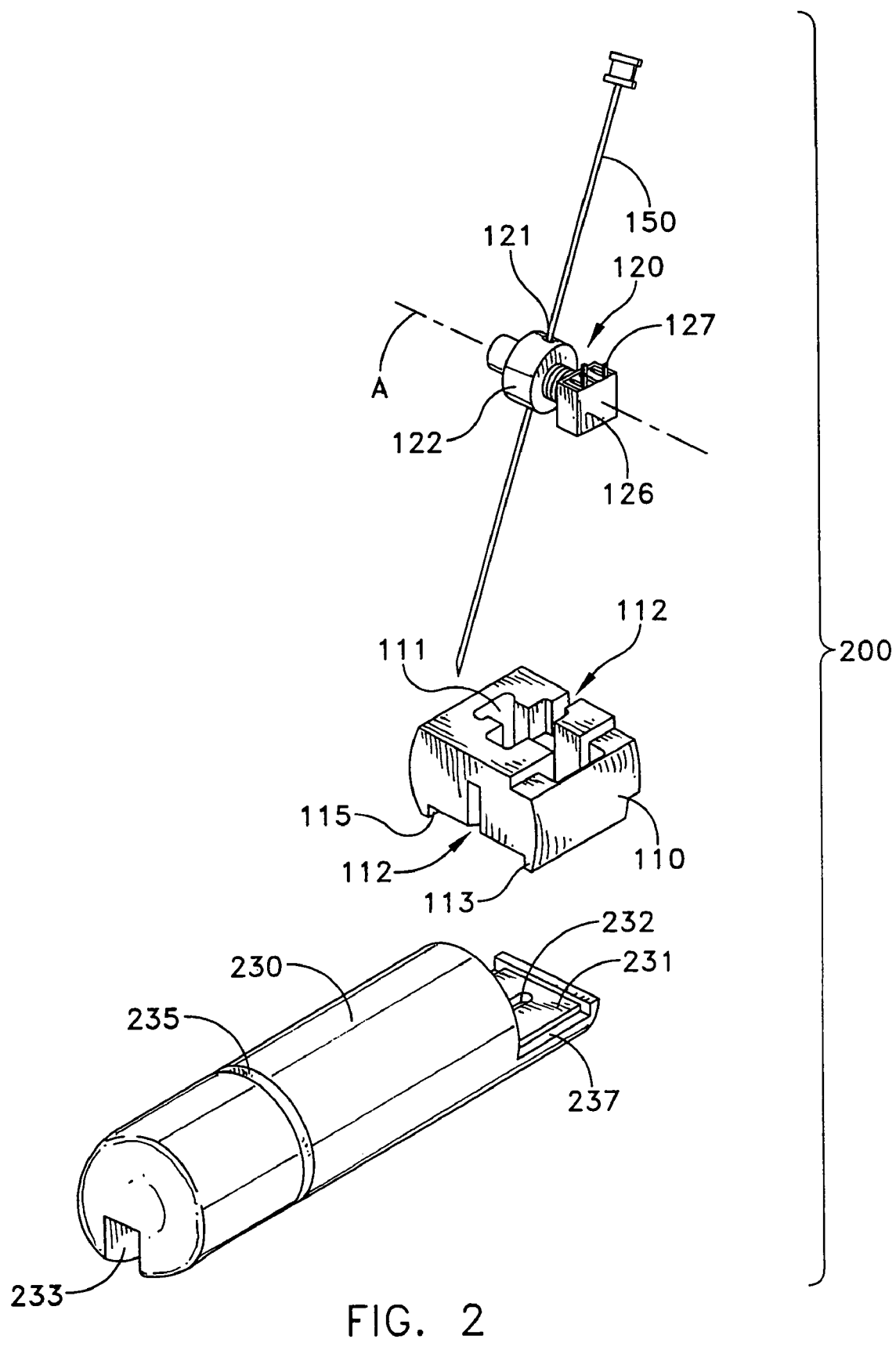
FIG. 2 is an exploded isometric view of a probe guide according to another embodiment of the invention.
Figure 2A:
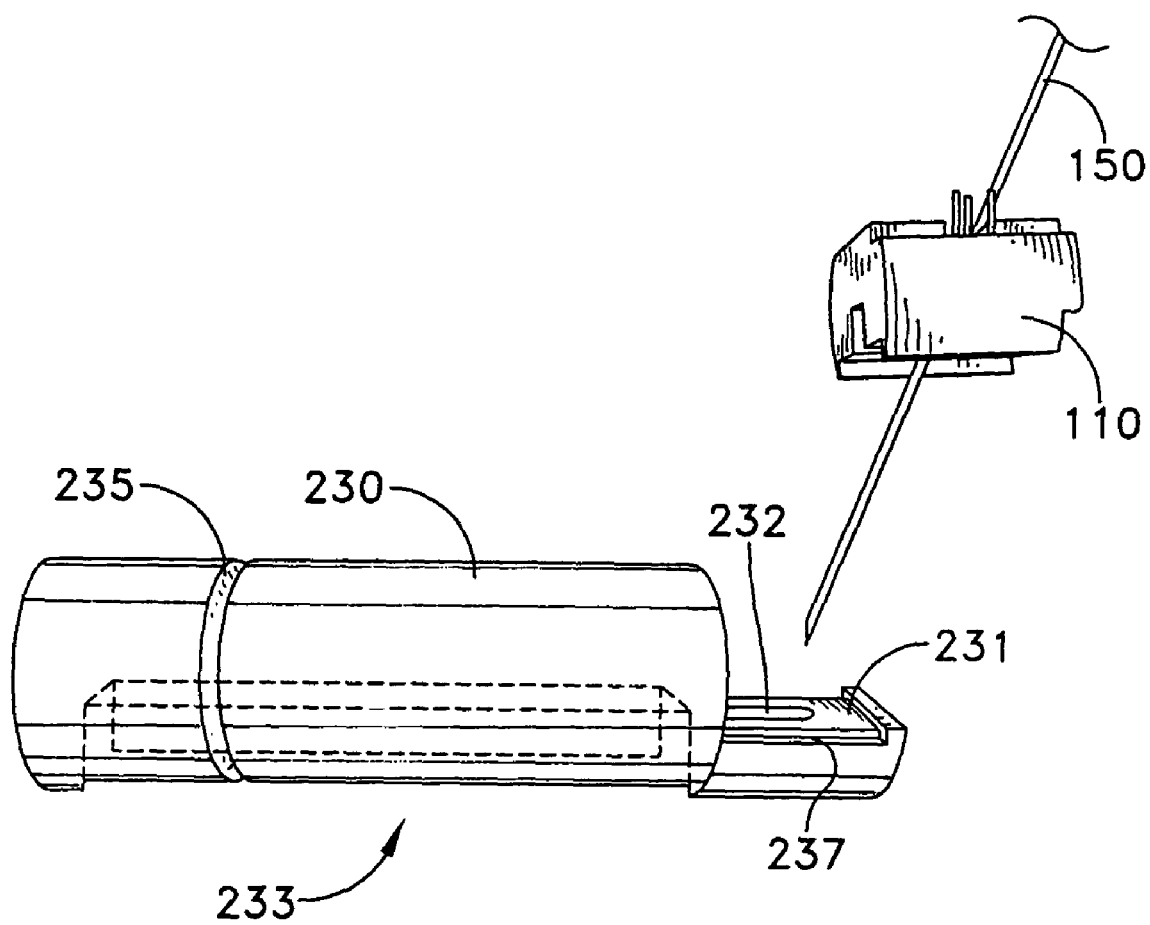
FIG. 2A is a side view of a probe guide body and a connecting member of the probe guide of FIG. 2.
Figure 2B:
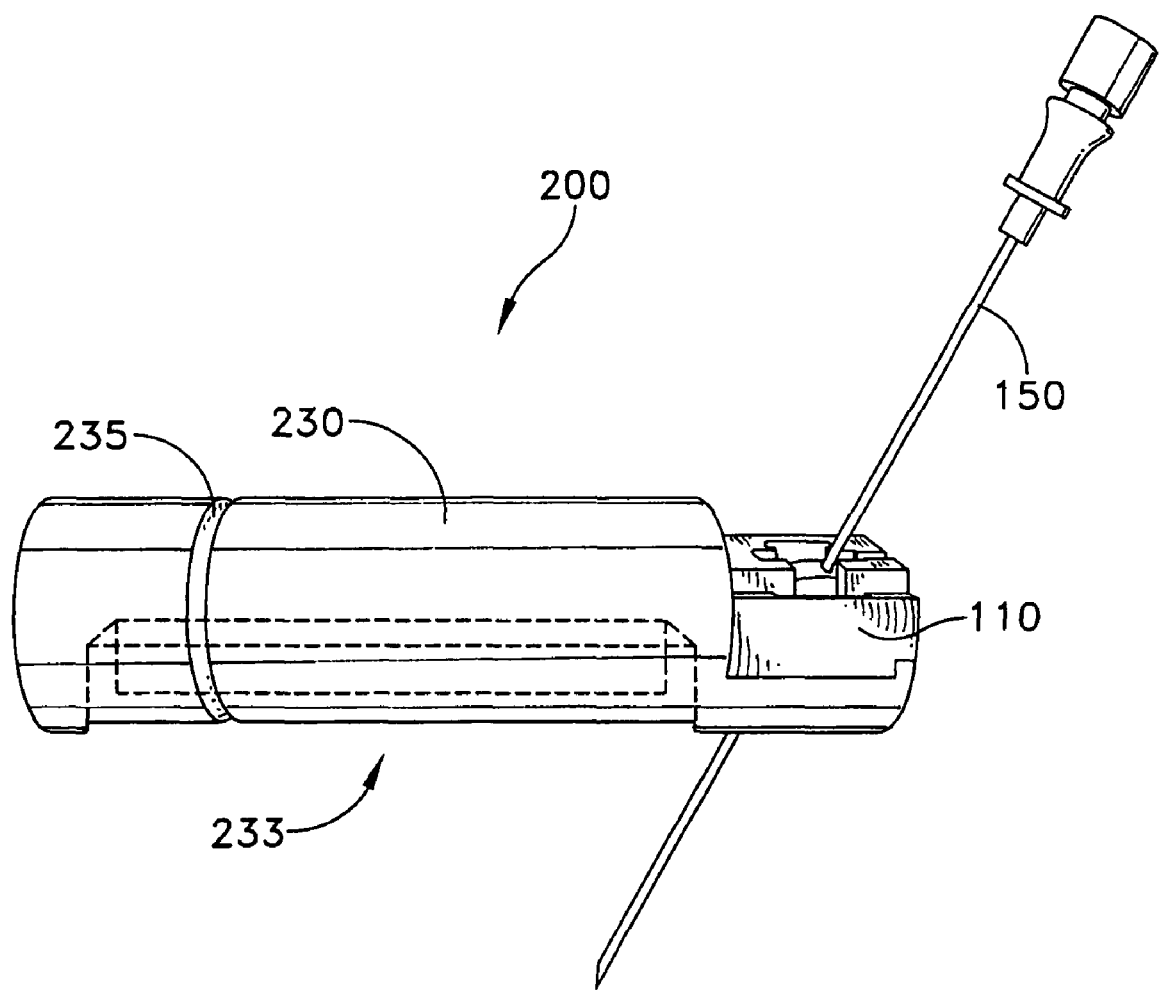
FIG. 2B is a side view of the probe guide body and the connecting member of FIG. 1A in an assembled form, a probe needle 150 being held within the probe guide body.
Figure 2C:
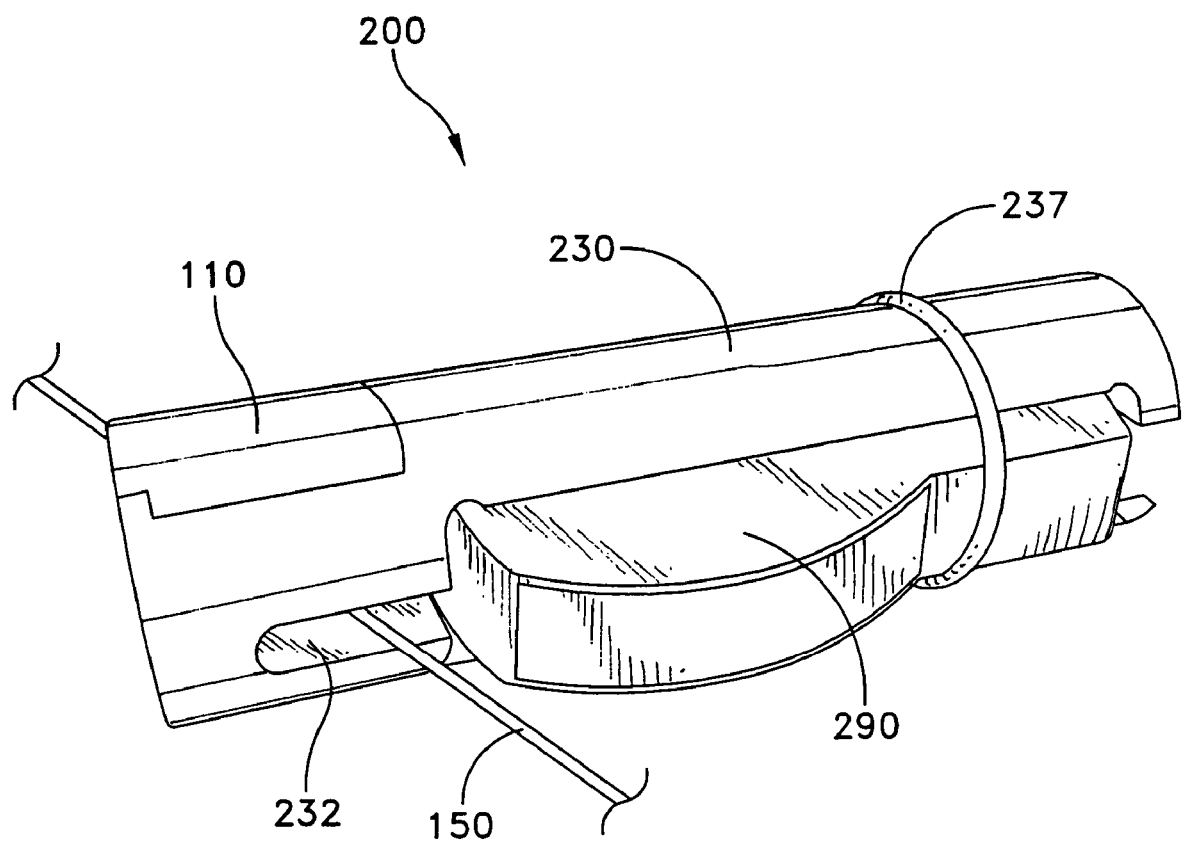
FIG. 2C is a isometric view of the fully assembled probe guide of FIG. 2 attached to an ultrasound transducer.
Figure 2D:
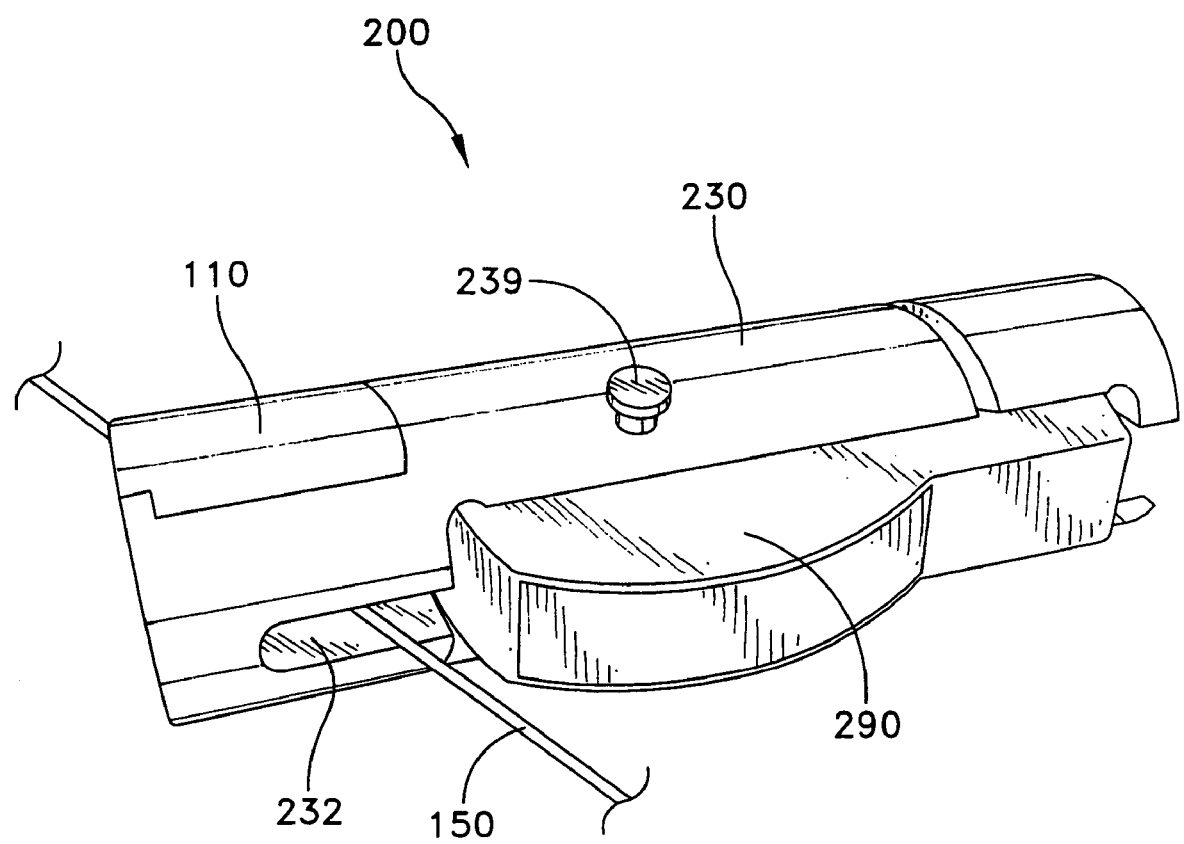
FIG. 2D is a isometric view of another embodiment of the fully assembled probe guide of FIG. 2 attached to an ultrasound transducer.

Referring to FIGS. 2 through 2D, a probe guide 200 according to another embodiment of the invention is disclosed. FIG. 2 is an exploded view of the probe guide 200. The probe guide 200 may include a probe guide body 110 and a connecting mechanism 230 for connecting the probe guide 200 to a medical imaging device 290 (shown in FIG. 2C). A probe holder 120 for holding a probe 150 is provided in the probe guide body 110. The probe guide body 110 and the probe holder 120 is the same as those corresponding structures discussed in reference to the embodiment of the invention illustrated in FIGS. 1 through 1F.

The connecting mechanism 230 is adapted and configured to connect the probe guide 200 to the medical imaging device 290, which in this example is an ultrasound transducer model B-K 8664. It is to be noted that medical imaging devices come in a variety of configurations. Therefore, the particular shape of the connecting mechanism 230 may be configured and adapted to adopt a shape that is appropriate for connecting to a particular medical imaging device used in a given application. In this embodiment of the invention, the connecting mechanism 230 is configured and adapted to connect to the medical imaging device 290, which for example, has a different physical configuration than the medical imaging device 190 illustrated in FIGS. 1E and 1F.

Referring to FIGS. 2 and 2A, the connecting mechanism 230 includes a base portion 231 for receiving the probe guide body 110. The base portion 231 may have side edges 237 along its sides (the side edge on the far side of the base portion 231 in FIG. 2 is not visible) for engaging the bottom flanges 113 and 115 of the probe guide body 110. FIG. 2B shows the probe guide body 110 and the connecting member 230 assembled together. Referring to FIGS. 2, 2A, and 2C, the connecting member 230 is provided with a channel 232 that corresponds with the channel 112 of the probe guide body 110 to accommodate the probe 150 and allow the probe 150 to be manipulated through its full range of angular orientations.

The connecting member 230 may be provided with a cavity 233 for receiving the medical imaging device 290. FIG. 2B illustrates a side elevational view of the fully assembled probe guide 200 including a biopsy probe needle 150. FIG. 2C is a is isometric view of the fully assembled probe guide 200 attached to the medical imaging device 290. The connecting mechanism 230 may be provided with a channel or a groove 235 along the outer surface of the connecting mechanism 230 for securing the medical imaging device 290 using an elastic band 237. It would be obvious to one of ordinary skill in the art that the connecting mechanism 230 maybe configured and adapted in many different ways to secure the medical imaging device 290. For example, in an embodiment shown in FIG. 2D, a set screw 239 that is threaded through the connecting mechanism 230 may be provided to secure the medical imaging device 290 in the chamber 233.

Figure 3:
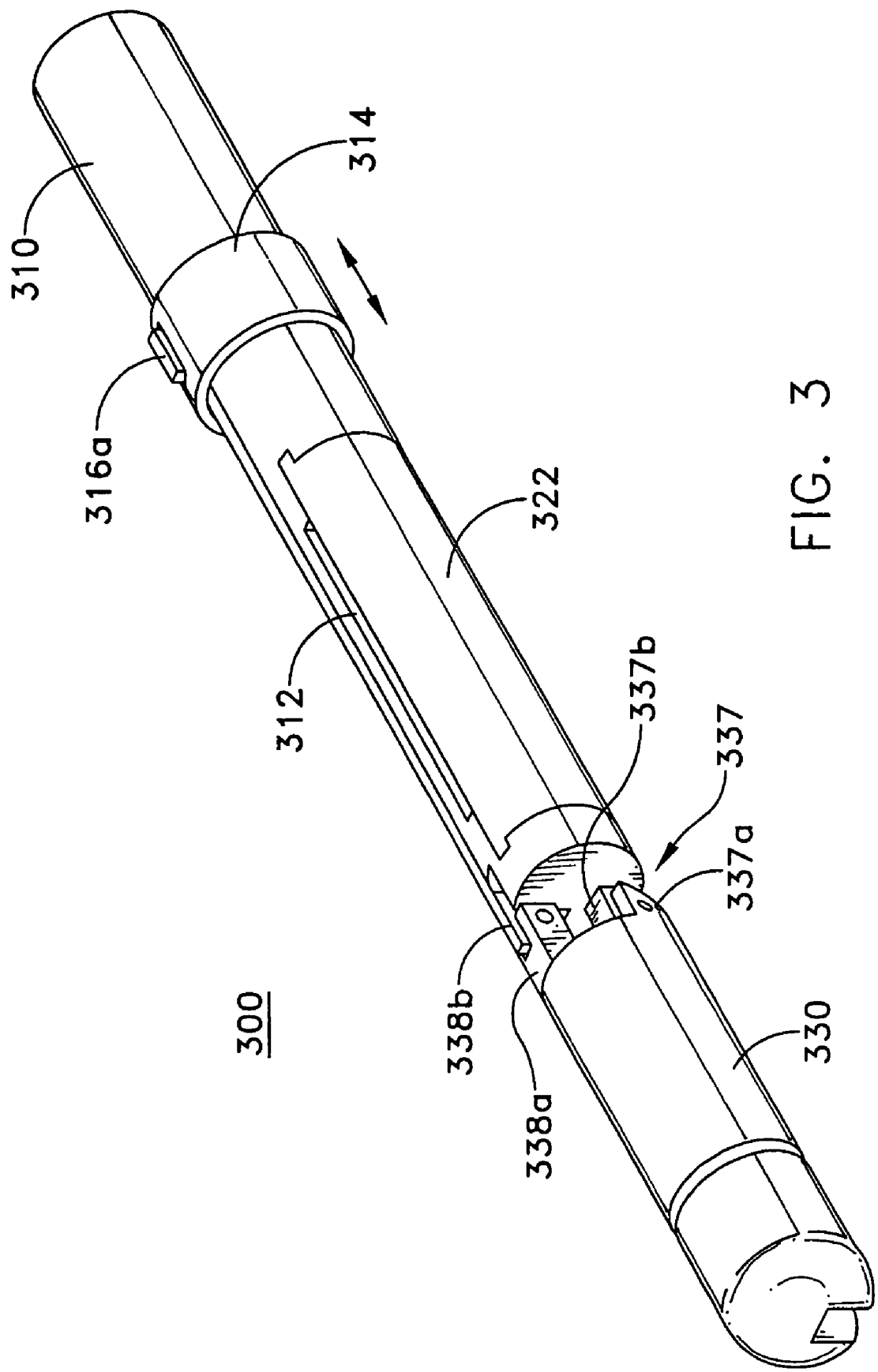
FIG. 3 is a isometric view of a fully assembled probe guide according to another embodiment of the invention.
Figure 3A:
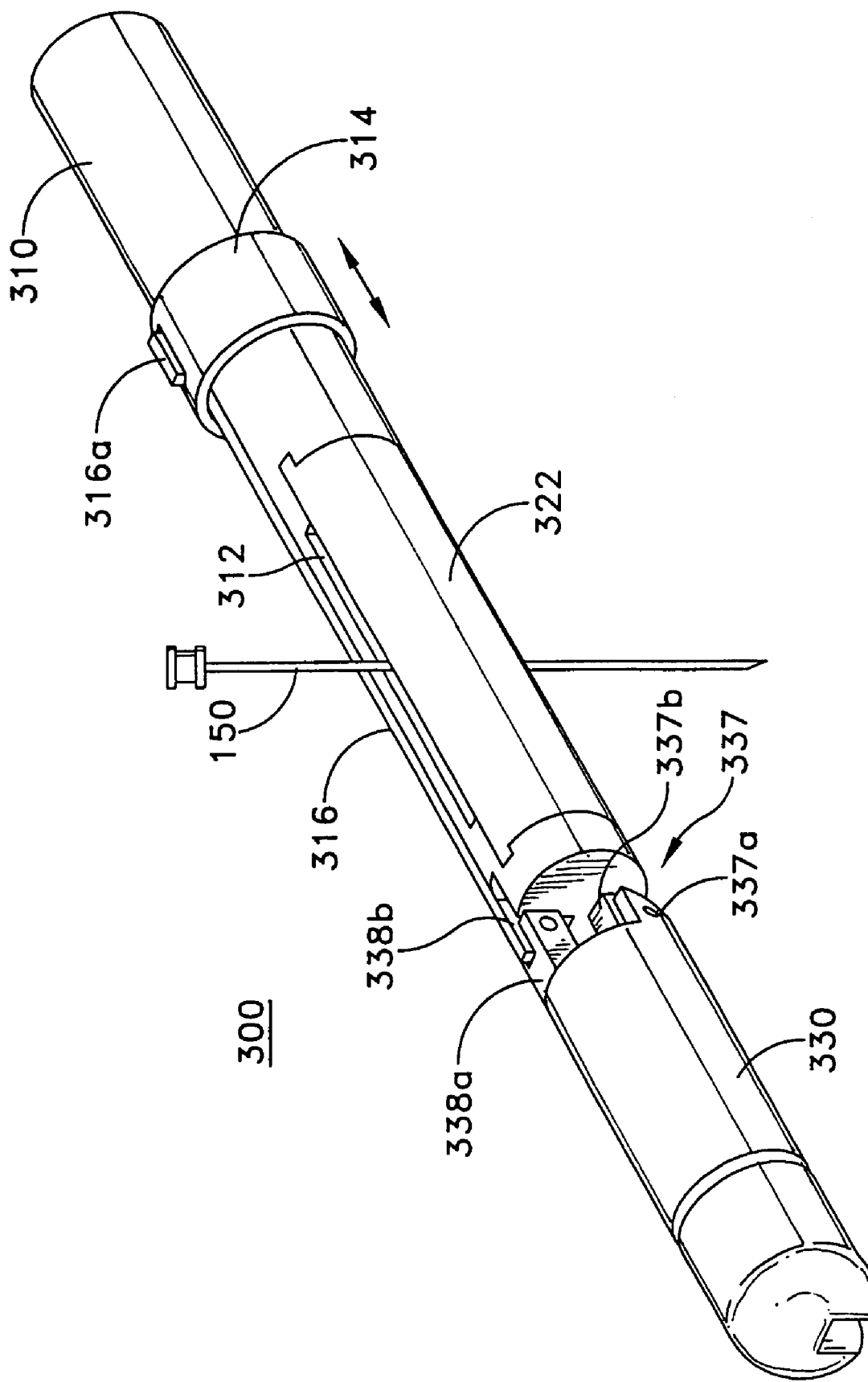
FIG. 3A is a isometric view of the probe guide of FIG. 3 holding a probe needle 150.
Figure 3B:
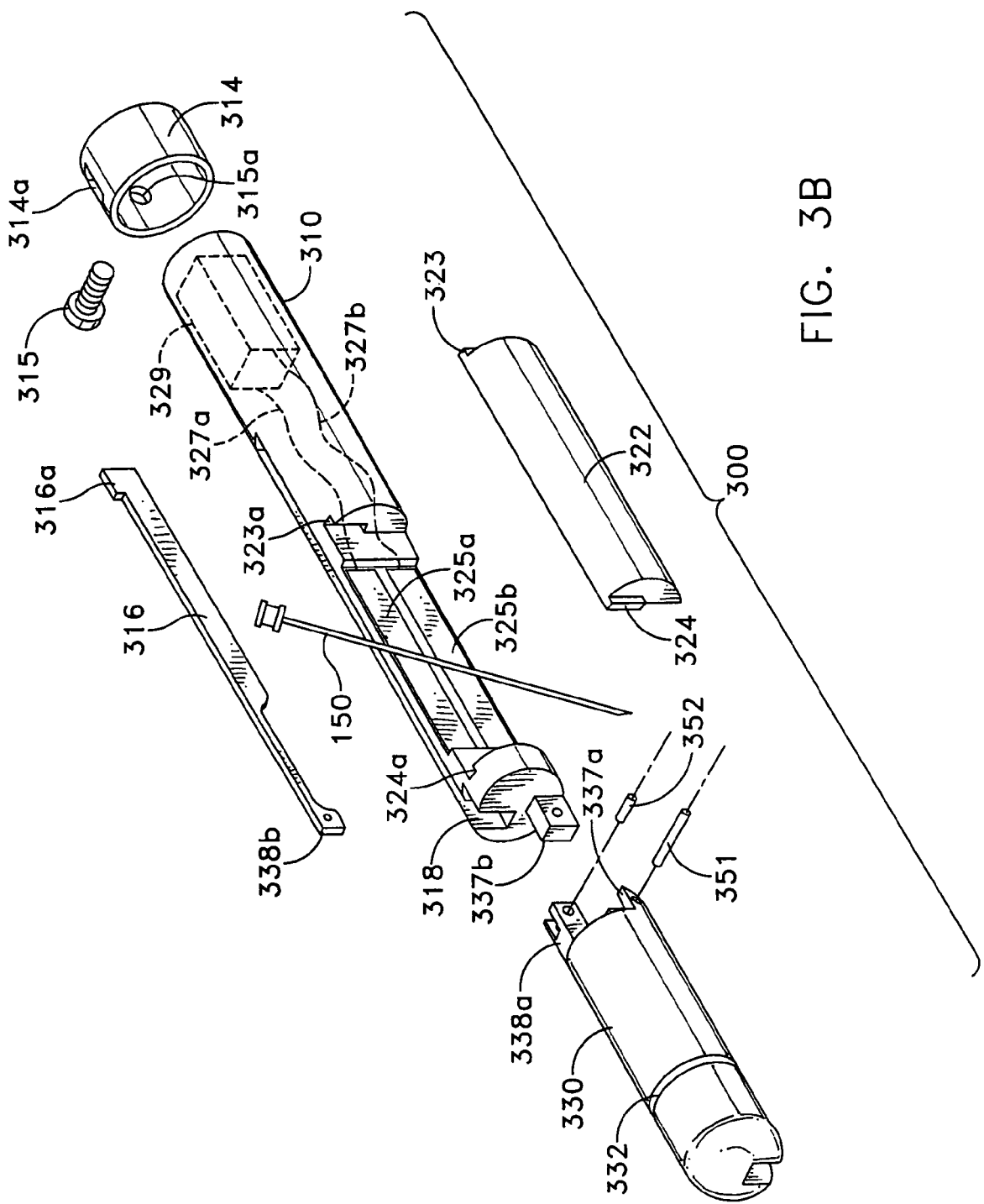
FIG. 3B is an exploded view of the probe guide of FIG. 3A.
Figure 3C:
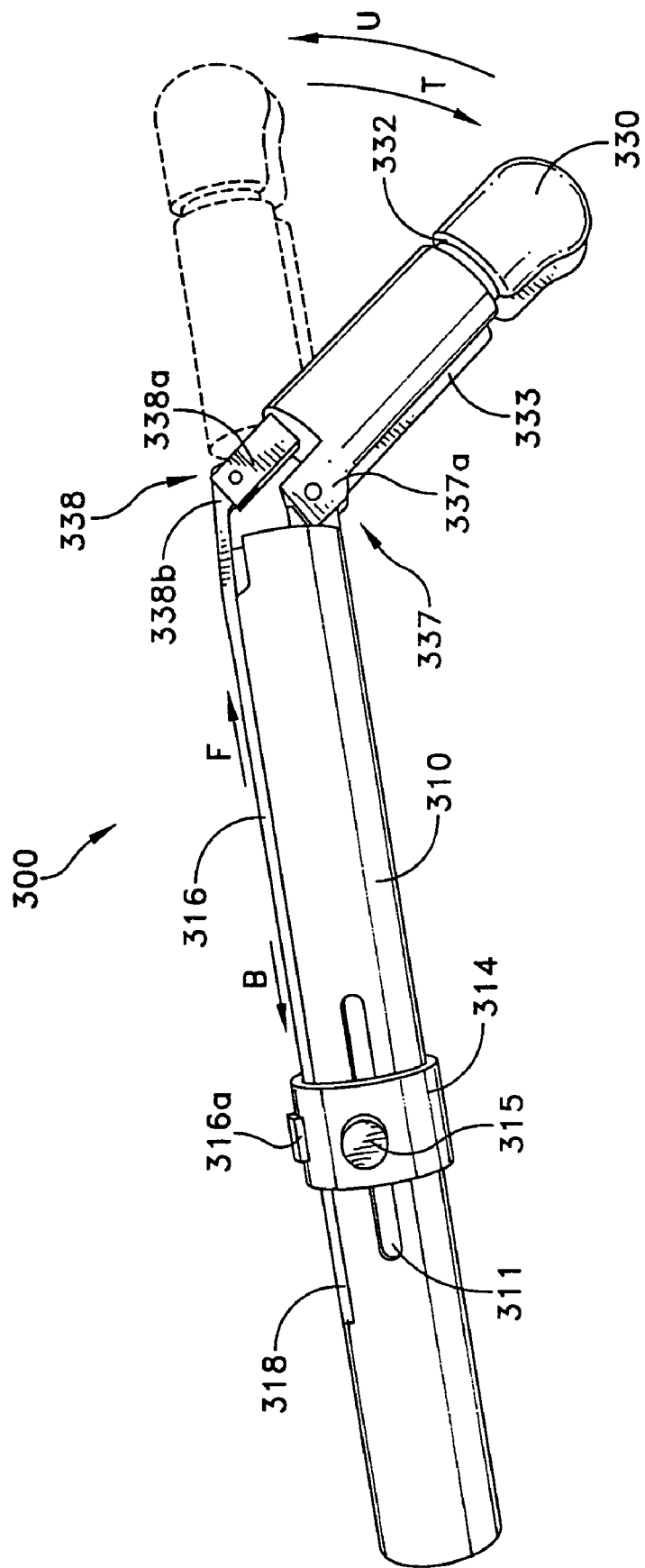
FIG. 3C is a side view of a fully assembled probe guide of FIG. 3 without a probe or a medical imaging device.
Figure 3D:
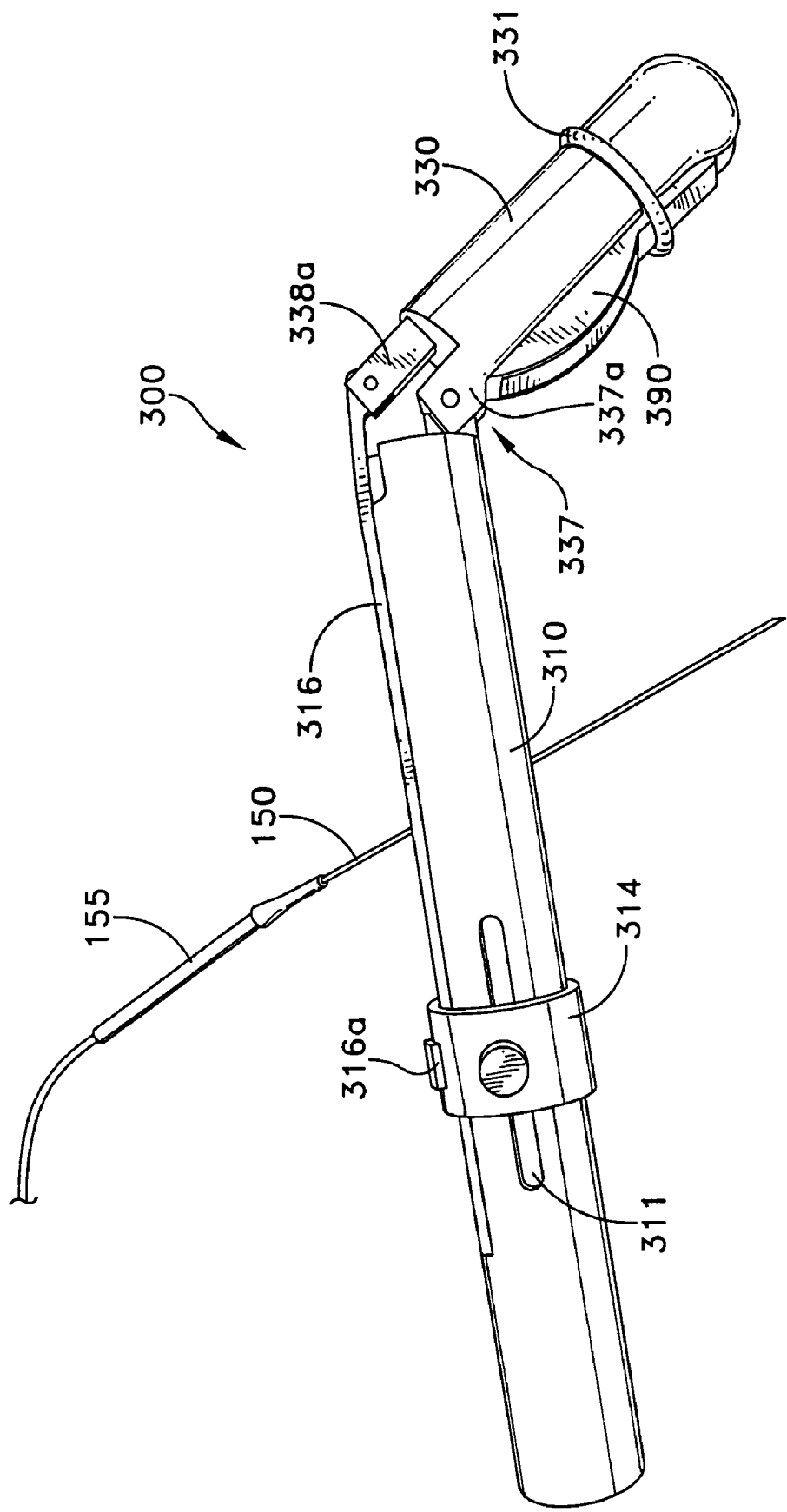
FIG. 3D is a side view of the probe guide of FIG. 3A with a probe needle 150 and a medical imaging device (ultrasound transducer) 390 in place.
Figure 3E:
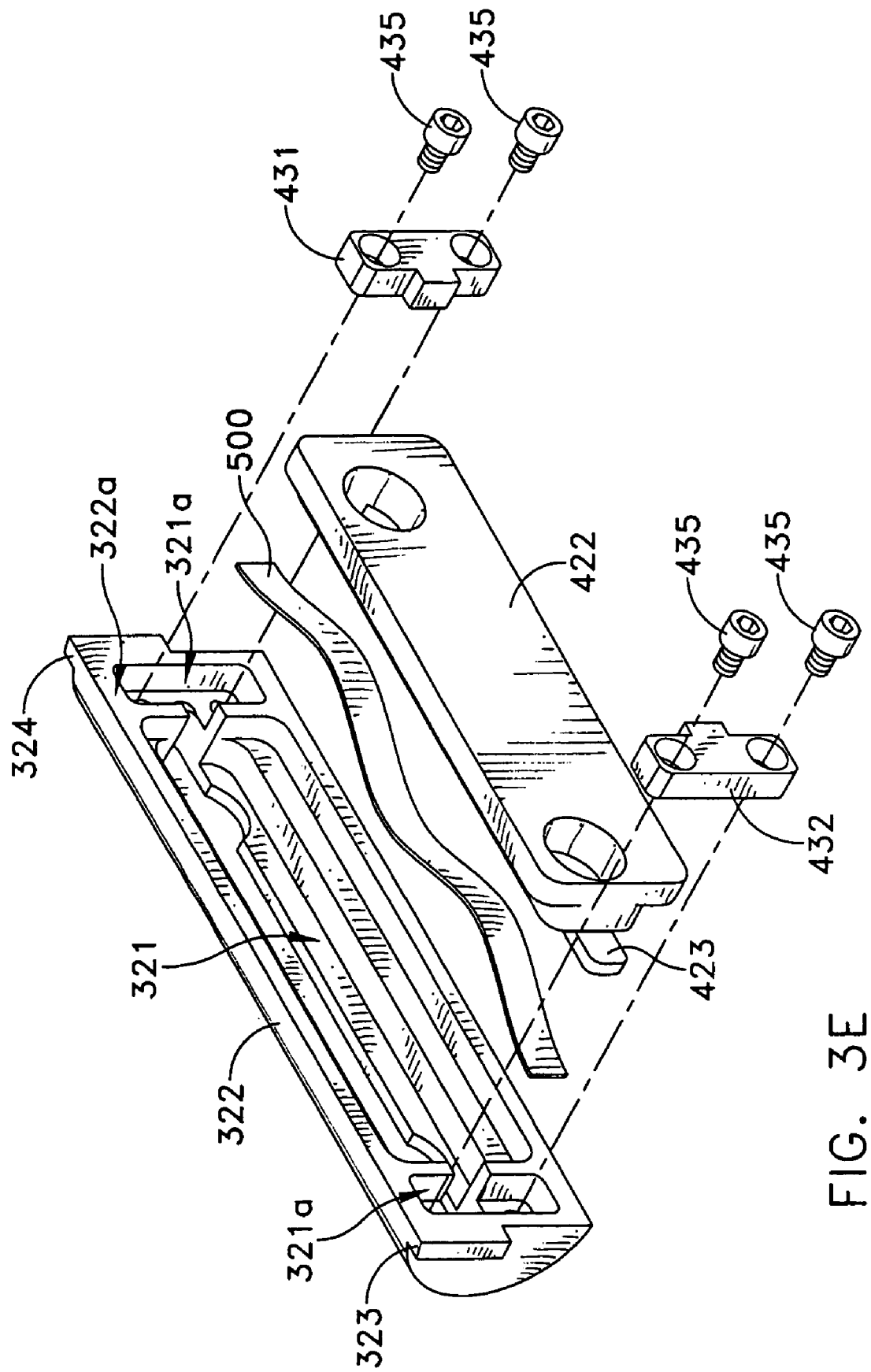
FIG. 3E is an exploded isometric view of the detachable probe holder 322.
Figure 3F:
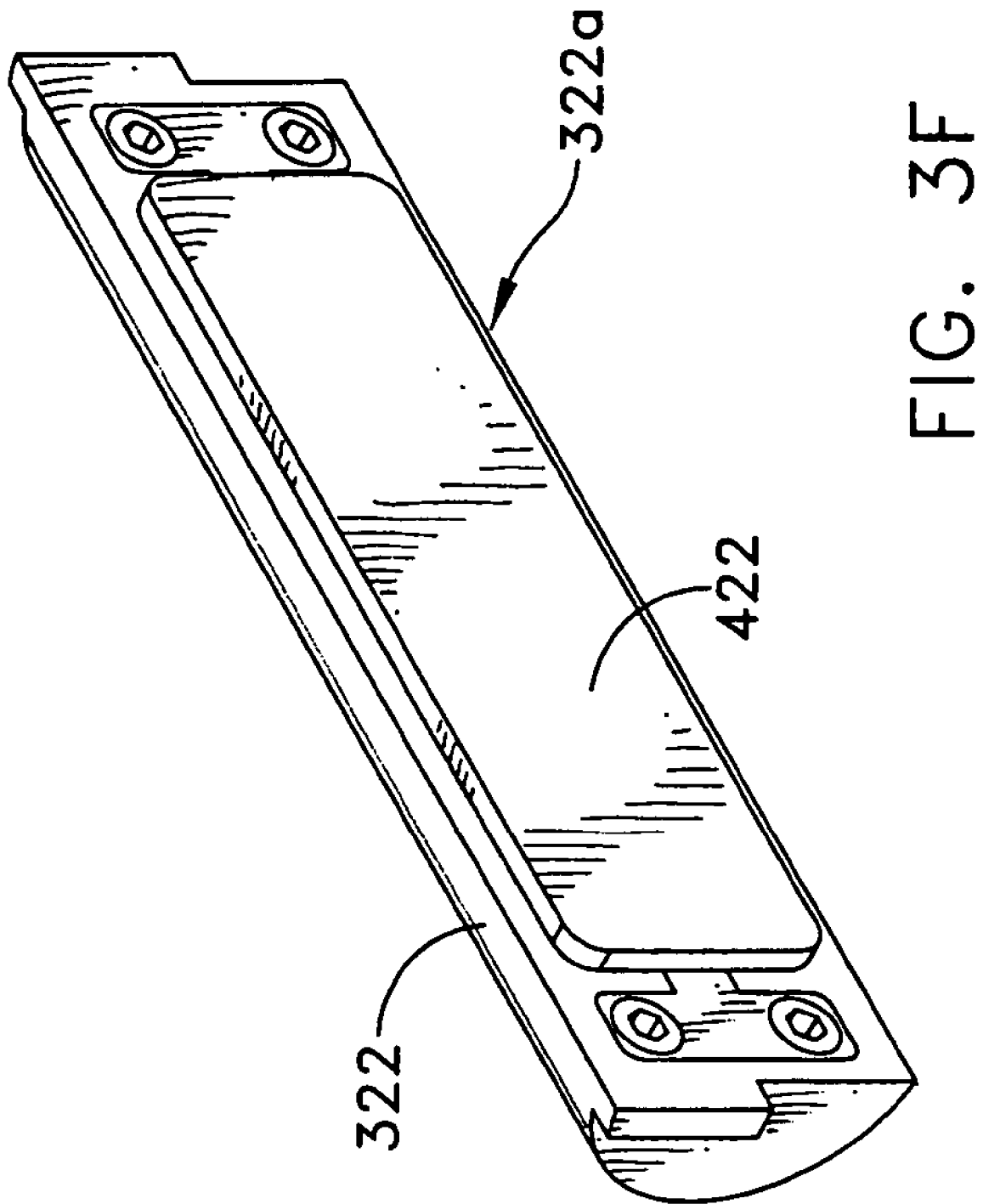
FIG. 3F is a isometric view of the fully assembled detachable probe holder 322.
Figure 30:
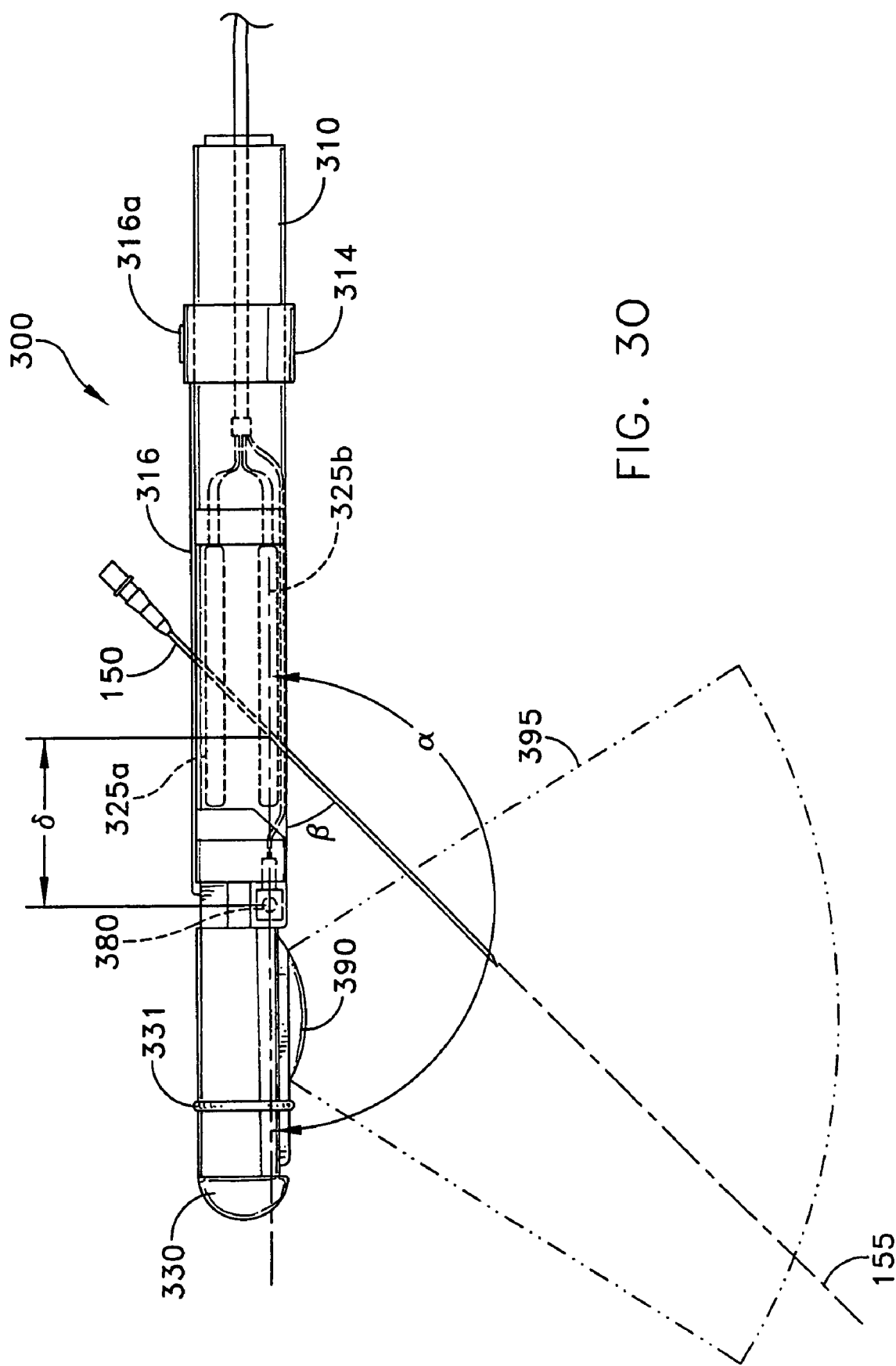
Figure 3P:
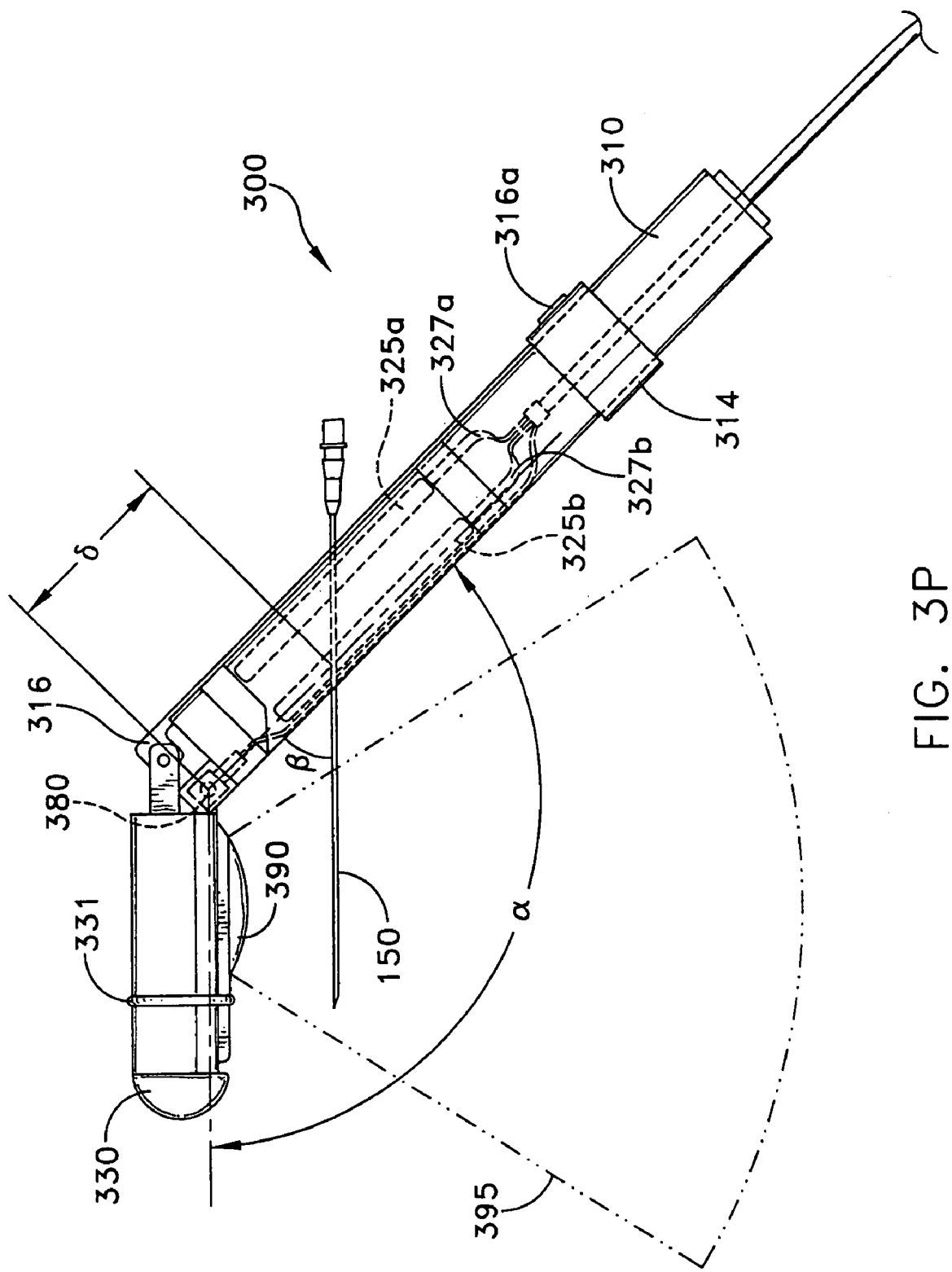
FIG. 3P is an illustration of the probe guide 300 of FIG. 3N with the probe guide 300 bent at an angle $\alpha$, where $90°<\alpha<180°$.
Figure 3Q:
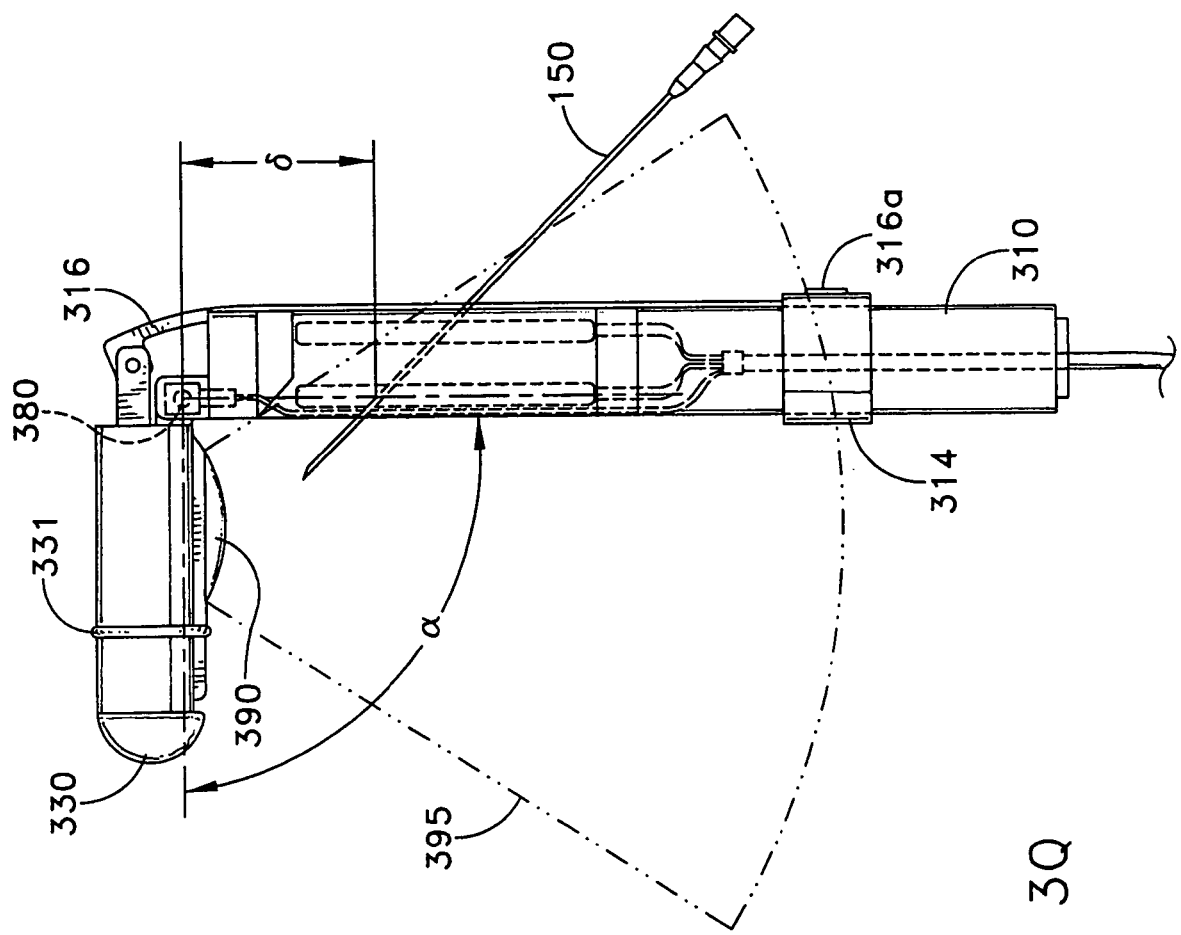
FIG. 3Q is an illustration of the probe guide 300 of FIG. 3O with the probe guide 300 bent at 90° angle.

Referring to FIGS. 3 through 3Q, according to yet another aspect of the invention, an articulating probe guide 300 for use in conjunction with a medical imaging device is disclosed. FIGS. 3 and 3A illustrate isometric views of a fully assembled probe guide 300. The probe guide 300 comprises a probe guide body 310 and a connecting mechanism 330 for connecting the probe guide 300 to a medical imaging device 390 (shown in FIG. 3D). In this exemplary embodiment, the probe guide body 310 and the connecting mechanism 330 have longitudinally extending, generally cylindrical structure. However the probe guides of the invention are not limited to cylindrical structures and it would be obvious to one skilled in the art to modify the general shape of the probe guide for aesthetical reasons as well as to accommodate the requirements of a particular application.

The probe guide body 310 and the connecting mechanism 330 are connected to each other by a hinge mechanism 337 allowing the probe guide body 310 and the connecting mechanism 330 to be hingeably connected to each other. In this embodiment of the invention, the hinge mechanism 337 is formed by a first hinge member 337a provided on the connecting mechanism 330 and a corresponding second hinge member 337b provided on the probe guide body 310. The first hinge member 337a mates with the second hinge member 337b to form the hinge mechanism 337.

As shown in the exploded view of FIG. 3B, a hinge pin 351 is inserted through the first and second hinge members 337a and 337b. The hinge mechanism 337 allows the probe guide 300 to be bent at the hinge so that the angular relationship between the probe guide body 310 and the connecting mechanism 330 may be articulated. This, in turn, controls the position of the probe 150 held by the probe guide body 310 may be adjusted in relation to the image plane 395 (see FIGS. 3N-3P) of the medical imaging device 390. This provides the first degree of freedom for the probe 150 in relationship to the medical imaging device 390.

A various mechanical configuration may be utilized to lock the angular orientation of the connecting mechanism 330 and the probe guide body 310. In this embodiment of the invention, an articulation control arm 316 is provided in the probe guide body 310 for this purpose. The control arm is an elongated member having a hinge-forming head portion 338b and a tail portion 316a. The probe guide body 310 has a longitudinally oriented slot 318 in which the control arm 316 sits in a slidable manner. The head portion 338b of the control arm 316 mates with a hinge member 338a provided on the connecting mechanism 330 to form a second hinge mechanism 338. Furthermore, a retainer ring 314 is provided as a control arm locking mechanism for controlling and locking the position of the control arm 316. The retainer ring 314 circumscribes the probe guide body 310 and the tail portion 316a of the control arm 316 protrudes through an opening 314a in the retainer ring 314. This arrangement allows the user to adjust the angular orientation of the connecting member 330 by sliding the retainer ring 314 along the probe guide body 310 in a longitudinal direction. Sliding the retainer ring 314 causes the control arm 316 to slide within the slot 318 which, in turn, manipulates the angle of the connecting mechanism 330. For example, sliding the retainer ring 314 in direction F shown in FIG. 3C will push or slide the control arm 316 in the same direction. This sliding motion of the control arm 316 pushes against the hinge member 338a causing the connecting mechanism 330 to bend downwardly, pivoting about the pivoting axis of the hinge mechanism 337, as shown by the arrow T. On the other hand, sliding the retaining ring 314 in direction B shown in FIG. 3C will pull the control arm 316 in the same direction. This, in turn, will pull on the hinge member 338a causing the connecting mechanism 330 to pivot about the pivoting axis of the hinge mechanism 337 in directoin shown by the arrow U. Thus, the retainer ring 314 is generally used to adjust the position of the connecting mechanism 330 within its full range of position. In a preferred embodiment of the invention, the full range of position includes the probe guide 300 being in a straight configuration illustrated in FIG. 3 to the 90° configuration illustrated in FIG. 3P.

To fix or lock the angular configuration of the connecting mechanism 330, the retainer ring 314 may be provided with a set screw 315 which threads into the screw hole 315a in the retainer ring 314. The probe guide body 310 may be provided with a groove 311 into which the set screw 315 extends to prevent the retainer ring 314 from rotating about the probe guide body 310 and substantially limit the motion for the retainer ring 314 to linear motion along the longitudinal directions F and B illustrated in FIG. 3C. The position of the retainer ring 314 may be fixed by tightening the set screw 315 into the groove 311.

Referring to FIGS. 3 and 3A, a longitudinally oriented slot 312 is provided in the probe guide body 310 to hold a probe 150 in the probe guide body 310. The slot 312 is defined by the probe guide body 310 and a detachable probe holder 322. As illustrated in the exploded view of FIG. 3B, the detachable probe holder 322 is attached to the probe guide body 310 by sliding flanges 323 and 324 into guide grooves 323a and 324a provided in the probe guide body 310. The probe 150 is held in the slot 312 by the compressive force exerted by the detachable probe holder 322 pressing the probe 150 against the probe guide body 310.

FIGS. 3E-3L are detailed illustrations of the detachable probe holder 322 and its components. The inner side 322a of the detachable probe holder 322, which form one side of the slot 312 and faces the probe 150, has provided therein a spring loaded face plate 422 that exerts the compressive force against the probe 150 held within the slot 312. The inner side 322a of the detachable probe holder 322 is provided with a main cavity 321 and side cavities 321a for accommodating the face plate 422 and brackets 431 and 432. The face plate 422 sits within the cavity 321 and secured in place by brackets 431 and 432.

The face plate 422 may be provided with flanges 423 and 424 such that when the face plate 422 sits within the cavity 321 of the detachable probe holder 322, the flanges 423 and 424 protrudes into the side cavities 321a of the detachable probe holder 322. A spring member 500 is provided inside the cavity 321 between the probe holder 322 and the face plate 422 for providing the compressive force. The brackets 431 and 432 secure the face plate 422 to the detachable probe holder 322 in such a manner so that they allow the face plate 422 to float on the spring member 500 while functioning as stops preventing the face plate 422 from falling out of the cavity 321. The brackets 431 and 423 may be secured to the probe holder 322 using screws 435.

Illustrated in FIG. 3F, is an assembled detachable probe holder 322. At rest state, the face plate 422 is biased by the spring 500 and protrudes out of the surface of the inner side 322a. When the detachable probe holder 322 is secured to the probe guide body 310 and the probe 150 is inserted into the slot 312 (defined by the detachable probe holder 322 and the probe guide body 310), the face plate 422 exerts a force on to the probe 150 holding the probe 100 between the probe holder 322 and the probe guide body 310. Preferably, the force exerted on the probe 150 is sufficiently high to prevent the probe 150 from any unwanted movement within the probe guide body 310 but still allow the probe 150 to be manipulated by the user to adjust the position of the probe 150. The probe's movement within the slot 312 has two degrees of freedom, angular and axial translations, within the image plane. For example, the probe 150 should remain in place and maintain its position and not displaced by external jarring forces encountered in typical application environments, such as being bumped by the patient or the medical personnel. However, the medial personnel using the system should be able to move and manipulate the probe 150 to adjust its position. A spring member 500 having an appropriate spring force may be selected to achieve the desired result.

According to an aspect of the invention, the probe guide system of the invention extrapolates the penetration path 155 of the probe 150 in a medical procedure, such as a biopsy, based on its position and orientation before the probe 150 is inserted into the patient's body. To achieve this functional aspect of the probe guide system using the probe guide 300, a first encoder 360 may be incorporated into hinge mechanism 337. The first encoder 360 is used for detecting or measuring the relative angular relationship of the connecting mechanism 330 and the probe guide body or the probe guide body 310. This angle is represented by $\alpha$ in FIGS. 3O-3Q. A second encoder 325 is provided in the probe guide body 310 for detecting or measuring the angular orientation of the probe 150 relative to the probe guide body 310. This angle is represented by $\beta$ in FIGS. 3O-3Q.

The angle $\beta$ and the linear position $\delta$ of the probe 150 are measured or detected by the second encoder 325. The second encoder 325 comprises two sensor strips 325a and 325b as illustrated in FIG. 3B provided on the surface of the probe guide body 310 facing the inner surface 322a of the detachable probe holder 322. Thus, when the probe 150 is inserted into the slot 312 defined by the probe holder 322 and the probe guide body 310, the probe 150 presses against the sensor strips 325a and 325b. Each of the sensor strips 325a and 325b are pressure sensing resistance type encoders. The sensor strips 325a and 325b are pressure activated devices whose resistance varies depending on where along their lengths an applied pressure is detected. The pressure sensing technology applied to these sensor strips are similar to the technology used in other known devices such as computer touch pads. But, unlike the touch pad pointer devices found on computers, the sensor strips 325a and 325b are one dimensional and detects the position of the pressure point along the longitudinal axis of the sensor strips.

FIG. 3M illustrates the two sensor strips 325a and 325b with the probe 150 pressing against them. The contact points X and Y represents the pressure points formed by the probe 150 on the sensor strip 325a and 325b, respectively. The location of the contact points X and Y are determined by monitoring the electrical resistance of the sensor strips via the electrical connections 327a and 327b, respectively. FIG. 3N is a cross-sectional view of the sensor strip 325a taken along line A-A. The sensor strips 325a comprises a layer of compressible insulating gel 345 sandwiched between two conducting layers 342 and 343. At the contact point X under the probe 150, the conducting layers 342 and 343 make contact. And the electrical resistance between the conducting layers 342 and 343, measured through the conducting wires 327a, will vary depending on where along the length of the sensor strip 325a the contact point X is. The sensor strip 325b works in the same way as the sensor strip 325b. Thus, by monitoring the electrical resistance of the sensor strips 325a and 325b, through the electrical connectors 327a and 327b, respectively, one can determine the locations of the contact points X and Y. And as illustrated in FIG. 3M, by knowing the positions of the contact points X and Y, represented by distances $\delta 1$ and $\delta 2$ the angle $\beta$ may be determined. Because the sensor strips 325a and 325b are parallel and the spacing between them is known, the calculation of the angle $\beta$ is a matter of simple geometry and will not be explained here in detail.

Because the medical imaging device 390, and thus its image plane 395, is affixed to the connecting mechanism 330, by knowing the angles $\alpha$ and $\beta$, and the linear position $\delta$ of the probe 150 on the probe guide body 310, the penetration path 155 of the probe 150 can be extrapolated. The probe guide 300 is generally incorporated in a system having a processing unit that will generate a graphical representation of the penetration path 155 of the probe 150 and superimpose it onto the image plane 395 and display the output image on a display unit. In one embodiment, the probe guide 300 is connected to an ultrasound probe. The ultrasound probe is connected to a conventional ultrasound imaging unit displaying the ultrasound image. The output signals from the first and second encoders 360, 325 of the probe guide 300 are sent to the processing unit via an electrical connection.

As mentioned above, the processing unit converts the output, signals from the first and second encoders 360, 325, and extrapolates the penetration path 155 of the probe 150. The processing unit is connected to the ultrasound imaging unit and receives the cross-sectional ultrasound image through a video input port. The processing unit then superimposes the extrapolated penetration path 155 of the probe 150 over the cross-sectional ultrasound image and displays the composite image on display unit. The processing unit is provided with appropriate data processors and necessary software to carry out the data processing and calculations mentioned herein. The ability to extrapolate the penetration path 155 of the probe 150 and view it superimposed on to the cross-sectional image of the patient is very useful because the medical personnel using the system can adjust the probe's position and attitude by observing the extrapolated penetration path 155 on the display unit 510 until the penetration path 155 intersects with the target location (such as a suspected tumor for biopsy, etc.) before the probe 150 is inserted into the patient.

The probe guide 300 of the invention allows accurate placement of a probe, such as a biopsy needle, by allowing a range of both angular and lateral translation of the probe. Thus, the probe guide 300 provides a significant improvement over the conventional probe guides even without its ability to extrapolate and display the penetration path of the probe.

Figure 3R:
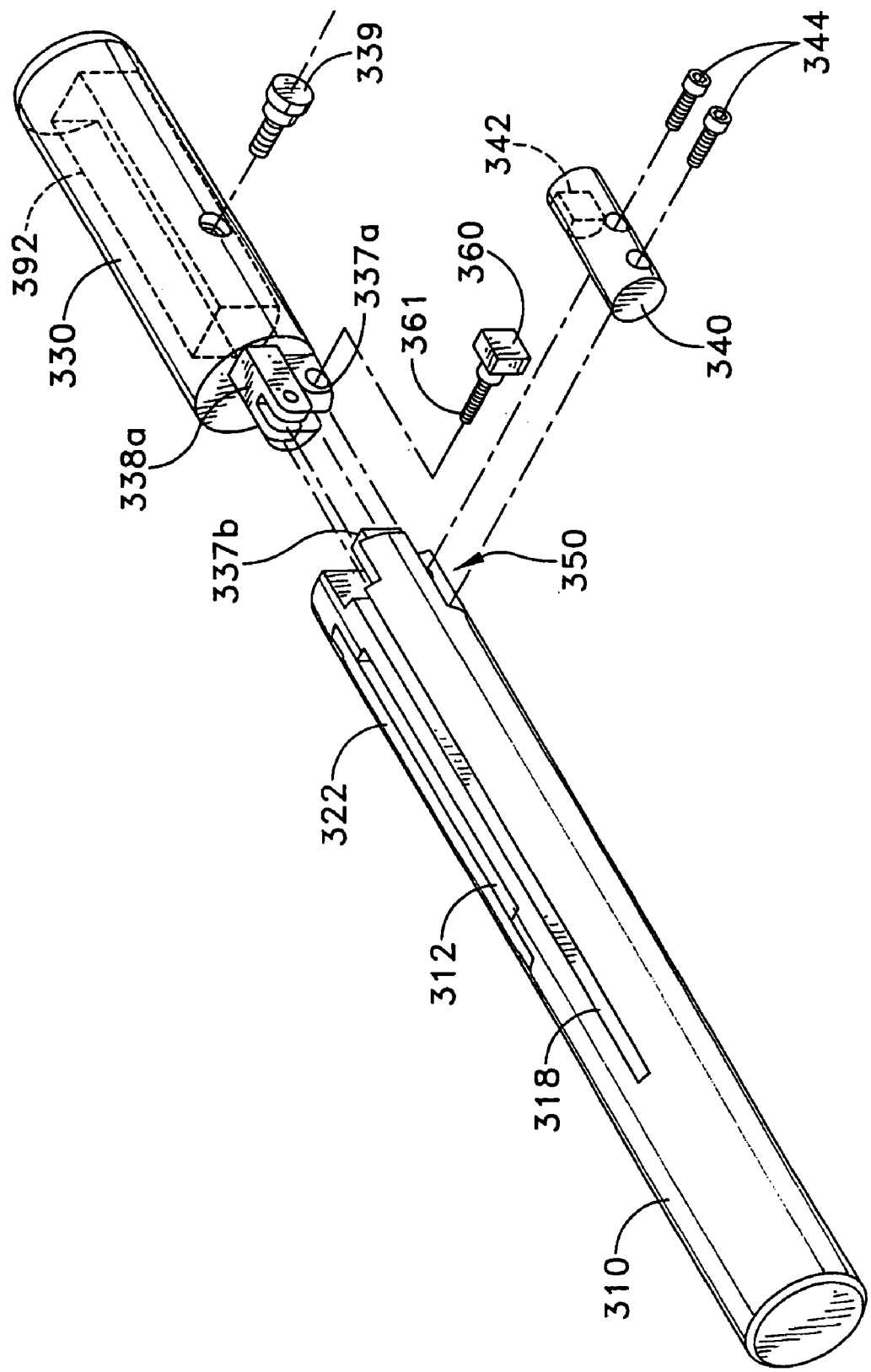
FIG. 3R is an exploded isometric view of the probe guide 300.

FIG. 3R is an exploded view of the probe guide 300 illustrating an exemplary configuration of the probe guide body 310 and the connecting mechanism 330 showing how the first encoder 360 may be incorporated into the hinge mechanism 337. The first encoder 360 may be a rotational potentiometer-type encoder that converts a rotational movement of the potentiometer into variable resistance output that is proportional to the angular translation of the encoder. The first encoder 360 has a stem portion 361 that is inserted through the first and second hinge members 337a and 337b instead of the hinge pin 351 shown in FIG. 3B. The first encoder 360 may have a square shaped head which is held in place by a retaining member 340. The retaining member 340 is secured to the probe guide body 310 by screws 344 and also has a cavity 342 that is shaped to engage the square shaped head of the first encoder 342. This engagement between the first encoder 360 and the retaining member 340 allows the square shaped head of the encoder 360 to rotate about its stem portion 361 along with the probe guide body 310 as the probe guide body 310 and the connecting mechanism 330 are bent about the hinge mechanism 337. The first encoder 360 may be a potentiometer-type whose electrical resistance changes proportionally with the angular orientation of its square-shaped head. Thus, by monitoring the electrical resistance of the first encoder 360, the angle α between the probe guide body 310 and the connecting mechanism 330 can be determined.

It should be noted that the probe guide embodiments 100 and 200 also may be used in conjunction with a processing unit that will, superimpose an extrapolated penetration path of the probe 150 on to the image fields generated by the ultrasound transducers 190 and 290. For example, referring to FIGS. 1 and 1E, because the rotational axis A of the probe 150 held in the probe guide 100 is fixed and known in relation to the ultrasound transducer 190, the encoder 126's output can be used to determine the angle θ. With the angle θ, the penetration path 155 of the probe 150 may be extrapolated and then superimposed on to the image field generated by the ultrasound transducer 190. In this set up, the ultrasound transducer 190 would be connected to an ultrasound imaging unit and the probe guide 100 would be connected to the processing unit and a display unit. Similarly, this concept can be applied to the probe guide 200 of FIGS. 2 through 2D.

In another embodiment, the probe guide 100 discussed in reference to FIGS. 1 through 1C may be used in an MRI imaging application. In this embodiment, rather than being attached to an ultrasound transducer 190, the probe guide 100 is used in conjunction with an MRI imaging system. The exemplary MRI system comprises a magnetic field ring. The probe guide 100 may be attached to an adaptor arm or other suitable fixture that allows the probe guide 100 to be positioned over a patient's body who is positioned in the magnetic field ring. The cross-sectional image generated by the MRI system is provided to the processing unit of the system via a video input connection. The output signal from the encoder 126 of the probe guide 100 is fed to the processing unit via an electrical connection. The output signal from the encoder 126 contains the information on the angular orientation of the probe 150 and the processing unit can determine the angular orientation of the probe 150 from the output signal received from the encoder 126. The adaptor arm is configured within the magnetic field ring such that the position of the probe guide 100 attached to the adaptor arm is always known to the processing unit of the system. This positional information for the probe guide 100 and the angular orientation of the probe 150, the processing unit can extrapolate the penetration path 155 of the probe 150. The processing unit superimposes the extrapolated penetration path 155 on to the MRI image received from the MRI system and may display the superimposed composite image on a display unit.

The structural components of the probe guides discussed herein may be made from medical grade and FDA approved materials. One example of such material that may be used to make the structural components of the probe guides 100, 200, and 300 discussed herein is medical grade Delrin® acetal resin.

While the foregoing invention has been described with reference to the above embodiments, various modifications and changes can be made without departing from the spirit of the invention. Accordingly, all such modifications and changes are considered to be within the scope of the appended claims.

What is claimed is:

1. An articulating probe guide for use in conjunction with a medical imaging device, the imaging device generating a cross-sectional image of a portion of a patient's body in an image plane, the articulating probe guide comprising:
   an imaging device holder having a connecting mechanism for connecting the imaging device holder to the imaging device;
   a probe guide body pivotally connected to the imaging device holder by a hinge;
   a probe holder for holding a probe provided in the probe guide body, the probe holder adapted and configured to allow angular and axial translations of the probe within the image plane when the imaging device holder is connected to the imaging device;
   a first encoder incorporated into the hinge for detecting angular orientation of the imaging device holder relative to the probe guide body; and
   a second encoder provided in the probe guide body for detecting angular orientation of the probe relative to the probe guide body and the liner position of the probe within the probe guide body;
   wherein the angular orientations of the imaging device holder and probe are used to extrapolate the probe's penetration path and superimpose the penetration path on to the cross-sectional image formed by the imaging device; and
   wherein the second encoder comprises at least two pressure sensitive sensor strips for detecting the angular orientation and liner position of the probe, and the probe holder comprises a spring loaded face plate for holding the probe between the face plate and the pressure sensitive sensor strips by exerting a lateral compressive force against the probe.

2. The articulating probe guide of claim 1, further comprising an articulation control arm and a control arm locking mechanism.

3. The articulating probe guide of claim 1, wherein the medical imaging device is an ultrasound transducer.

* * * * *